(12) United States Patent
Huang et al.

(10) Patent No.: US 6,887,875 B2
(45) Date of Patent: May 3, 2005

(54) 2,5-DIARYPYRIMIDINE COMPOUNDS

(75) Inventors: Jianhua Huang, Waterford, CT (US); Kevin Hodggetts, Kilingworth, CT (US); Dario Doller, Wallingford, CT (US); Ping Ge, Durham, CT (US); Yasuchika Yamaguchi, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 63 days.

(21) Appl. No.: 10/154,482

(22) Filed: May 22, 2002

(65) Prior Publication Data

US 2003/0119844 A1 Jun. 26, 2003

Related U.S. Application Data

(60) Provisional application No. 60/297,483, filed on Jun. 12, 2001.

(51) Int. Cl.[7] .................... C07D 239/26; C07D 403/04; A61K 31/506; A61K 31/505; A61P 25/24

(52) U.S. Cl. ............................ 514/252.02; 514/255.05; 514/256; 514/269; 544/238; 544/242; 544/295; 544/296; 544/319; 544/322; 544/333; 544/334; 544/335

(58) Field of Search ...................... 514/252.02, 255.05, 514/256, 269; 544/238, 242, 295, 296, 333, 335, 319, 322, 334

(56) References Cited

U.S. PATENT DOCUMENTS

| | | | | |
|---|---|---|---|---|
| 3,660,404 A | * | 5/1972 | Otterstedt et al. | .......... 544/296 |
| 4,788,197 A | | 11/1988 | Wakabayashi et al. | ...... 544/336 |
| 6,107,297 A | * | 8/2000 | Kindon et al. | ......... 514/252.02 |
| 6,686,469 B2 | * | 2/2004 | Eberle et al. | ................ 544/319 |

FOREIGN PATENT DOCUMENTS

| | | | |
|---|---|---|---|
| CA | 2318368 AA | * | 8/1999 |
| JP | 2-243676 A | * | 9/1990 |
| WO | WO 2000066565 A1 | * | 11/2000 |

OTHER PUBLICATIONS

Zobel J. Psych. Res., vol. 34, 2000, 171–181.*
McCarthy, J.R. et al, Ann. Reports Med. Chem., vol. 34, pp. 11–20, 1999.*
N. Vinot et al., "Synthese de pyrazines," Bulletin De La Societe Chimque De France, No. 12, (1968) pp. 4970–4974.
V. Baliah & K. Pandiarajan, "Synthesis of Some 2,3–Dihydropyrazines, Pyrazines & Piperzines," Dept. of Chem., Annamalai University, Ammamalainagar 608101, pp. 73–75.
G. Alvernhe et al., Tetrahedron letters, vol. 21, Pergamon Press Ltd (1980), pp–1437–1440.
J. Chellappa et al., "PMR Sprectra of Some Substituted Pyrazines & 2,3–Dihyropyrazines," Indian Journal of Chemistry, vol. 21B, Aug. 1982, pp. 778–779.
Y. Akita et al., "Cross–coupling Reaction of Chloropyrazines with Acetylenes," Chem. Phar, Bull., vol. 43, No. 4, Aug. 1985, pp. 1447–1458.

(Continued)

Primary Examiner—Thomas C. McKenzie
(74) Attorney, Agent, or Firm—Peter F. Corless; John B. Alexander; Edwards & Angell, LLP

(57) ABSTRACT

Diarylpyrimidine compounds of Formula I are provided, wherein.

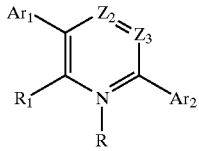

Formula I or a pharmaceutically acceptable salt thereof, wherein:

$Ar_1$ and $Ar_2$ are independently chosen from:
phenyl which is mono-, di-, or tri-substituted,
1-naphthyl and 2-naphthyl, each of which is optionally mono-, di-, or tri-substituted, and
optionally mono-, di-, or tri-substituted heteroaryl, said heteroaryl having from 1 to 3 rings, 5 to 7 ring members in each ring and, in at least one of said rings, from 1 to about 3 heteroatoms selected from the group consisting of N, O, and S;

R is oxygen or absent;

$Z_2$ is $CR_2$; $Z_3$ is nitrogen;

$R_1$ and $R_2$ are independently chosen from hydrogen, halogen, amino, cyano, nitro, optionally substituted alkyl, optionally substituted alkenyl, optionally substituted alkynyl, optionally substituted alkoxy, optionally substituted mono- or di-alkylamino, optionally substituted cycloalkyl, optionally substituted (cycloalkyl)alkyl, optionally substituted (cycloalkyl)oxy, optionally substituted (cycloalkyl)alkoxy, optionally substituted alkylthio, optionally substituted alkylsulfinyl, optionally substituted alkylsulfonyl, and optionally substituted mono- or dialkylcarboxamide; with the proviso that not all of $R_1$, $R_3$, and $R_4$ are hydrogen.

These compounds are useful in the treatment of a number of CNS and periphereal disorders, particularly stress, anxiety, depression, cardiovascular disorders, and eating disorders. Methods of treatments of such disorders and well as packaged pharmaceutical compositions are also provided.

Compounds of Formula I are also useful as probes for the localization of CRF receptors and as standards in assays for CRF receptor binding. Methods of using the compounds in receptor localization studies are given.

21 Claims, No Drawings

OTHER PUBLICATIONS

A. Ohta et al., "Coupling Reaction of Chloropyrazines and Their N–Oxides with Tetraphenyltin," Heterocycles, vol. 24, No. 3, 1986, pp. 785–792.

T. Benincori et al., "Studies on the Fischer Indole Synthesis: Rearrangements of Five–, Six– and Seven–membraned Cylic Hydrazones of Pyrazoline, Tetrahydropyridazine and Tetrahydro–1,2–diazepine Series in Polyphosphoric Acid," J. Chem. Soc. Perkin Trans., 1991, pp. 2139–2125.

A. Ohta et al., "Anti–Platelet Aggregation Activity of Some Pyrazines," Biol. Pharm. Bull. vol. 20, No. 10, 1997, pp. 1076–1081.

C. Yamagami et al., "Measurement and Production of Hydrophobicity Parameters for Highly Lipophilic Compounds: Application of the HPLC Column–Switching Technique to Measurement of log P of Diarylpyrazines," Journal of Pharm. Sciences, vol. 88, No. 12, 1999, pp–1299–1303.

On–lie Database Search identifying CAPLUS and MEDLINE using the phrase "diarylpyrazine," 2001.

On–lie Database Search identifying CAPLUS and MEDLINE using the phrase "arylpyrazines," 2001.

* cited by examiner

US 6,887,875 B2

2,5-DIARYPYRIMIDINE COMPOUNDS

This application claims the benefit of U.S. Provisional Application Ser. No. 60/297,483 filed Jun. 12, 2001, the teachings of which are incorporated herein by reference.

BACKGROUND

1. Field of the Invention

The present invention relates to 2,5-diarylpyridines, 2,5-diarylpyrazines, and 2,5-diarylpyrimidine compounds. Such compounds bind with high selectivity and/or high affinity to CRF1 receptors (Corticotropin Releasing Factor 1 Receptors). Preferred compounds of the invention block, inhibit, activate or otherwise modulate the activity of the receptors to which they bind. This invention also relates to pharmaceutical compositions comprising such compounds and to the use of such compounds in treatment of psychiatric disorders and neurological diseases, including major depression, anxiety-related disorders, post-traumatic stress disorder, supranuclear palsy and feeding disorders, as well as treatment of immunological, cardiovascular or heart-related diseases, irritable bowel syndrome, and colonic hypersensitivity associated with psychopathological disturbance and stress. Additionally this invention relates to the use such compounds as probes for the localization of CRF1 receptors in cells and tissues.

2. Background of the Invention

Corticotropin releasing factor (CRF), a 41 amino acid peptide, is the primary physiological regulator of proopiomelanocortin (POMC) derived peptide secretion from the anterior pituitary gland. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain. There is also evidence that CRF plays a significant role in integrating the response of the immune system to physiological, psychological, and immunological stressors.

CRF acts by binding to and modulating the signal transduction activities of specific cell surface receptors, including CRF1 receptors and CRF2 receptors. These receptors are found at high concentrations in the central nervous system (CNS), particularly in certain regions of the brain. CRF1 receptors are also found outside the CNS.

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system.

In affective disorder, or major depression, the concentration of CRF is significantly increased in the cerebral spinal fluid (CSF) of drug-free individuals. Furthermore, the density of CRF receptors is significantly decreased in the frontal cortex of suicide victims, consistent with a hypersecretion of CRF. In addition, there is a blunted adrenocorticotropin (ACTH) response to CRF (i.v. administered) observed in depressed patients. Preclinical studies in rats and non-human primates provide additional support for the hypothesis that hypersecretion of CRF may be involved in the symptoms seen in human depression. There is also preliminary evidence that tricyclic antidepressants can alter CRF levels and thus modulate the numbers of CRF receptors in brain.

The mechanisms and sites of action through which conventional anxiolytics and antidepressants produce their therapeutic effects remain to be fully elucidated. It has been hypothesized however, that they are involved in the suppression of CRF hypersecretion that is observed in these disorders.

CRF has been implicated in the etiology of anxiety-related disorders. CRF produces anxiogenic effects in animals and interactions between benzodiazepine/non-benzodiazepine anxiolytics and CRF have been demonstrated in a variety of behavioral anxiety models. Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test and in the acoustic startle test in rats. The benzodiazepine receptor antagonist Ro 15-1788, which was without behavioral activity alone in the operant conflict test, reversed the effects of CRF in a dose-dependent manner, while the benzodiazepine inverse agonist FG 7142 enhanced the actions of CRF.

CRF activity has also been implicated in the pathogeneisis of certain cardiovascular or heart-related, digestive, degenerative, dermatological, and immunological diseases, and disorders such as hypertension, tachycardia and congestive heart failure, stroke, acne, and osteoporosis, as well as in premature birth, psychosocial dwarfism, stress-induced fever, ulcer, diarrhea, post-operative ileus and colonic hypersensitivity, e.g., associated with psychopathological disturbance and stress.

SUMMARY OF THE INVENTION

The invention provides novel compounds of Formula I (shown below). The invention also comprises pharmaceutical compositions comprising compounds of Formula I and at least one pharmaceutically acceptable carrier or excipient. Such 2,5-diarylpyrazines, pyridines and pyrimidines bind to cell surface receptors, preferably G-coupled protein receptors, especially CRF receptors and most preferably CRF1 receptors. Preferred compounds of Formula I exhibit high affinity for CRF 1 receptors, i.e., they bind to, activate, inhibit, or otherwise modulate the activity of receptors other than CRF receptors with affinity constants of less than 1 micromolar, preferably less than 100 nanomolar, and most preferably less than 10 nanomolar. Additionally, preferred compounds of Formula I also exhibit high selectivity for CRF1 receptors.

The invention further comprises methods of treating patients suffering from certain diseases or disorders by administering to such patients an amount of a compound of Formula I effective to reduce signs or symptoms of the disease or disorder. These diseases and disorders include CNS disorders, particularly affective disorders, anxiety, stress, depression, and eating disorders and also include certain digestive disorders, particularly irritable bowel syndrome and Crohn's disease. These diseases or disorders further include cardiovascular or heart-related, digestive, degenerative, dermatological, and immunological diseases and disorders such as hypertension, tachycardia and congestive heart failure, stroke, acne and osteoporosis, as well as premature birth, psychosocial dwarfism, stress-induced fever, ulcer, diarrhea, post-operative ileus and colonic hypersensitivity. The patient suffering from such diseases or disorders may be a human or other animal (preferably a mammal), such as a domesticated companion animal (pet) or a livestock animal.

According to yet another aspect, the present invention provides pharmaceutical compositions comprising a compound of Formula I or a pharmaceutically acceptable salts or solvates thereof together with at least one pharmaceutically acceptable carrier or excipient, which compositions are useful for the treatment of the disorders recited above. The invention further provides methods of treating patients suffering from any of theses disorders with an effective amount of a compound or composition of Formula I.

Additionally this invention relates to the use of labeled compounds of Formula I (particularly radiolabeled compounds of this invention) as probes for the localization of receptors in cells and tissues and as standards and reagents for use in determining the receptor-binding characteristics of test compounds.

Thus, in a first aspect, the invention provides compounds of Formula I,

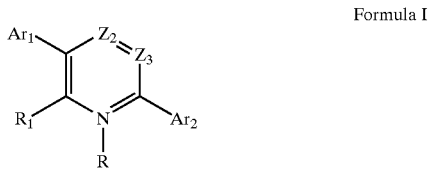

Formula I and the pharmaceutically acceptable salts thereof.

$Ar_1$ and $Ar_2$ are independently chosen from: phenyl which is mono-, di-, or tri-substituted, 1-naphthyl and 2-naphthyl, each of which is optionally mono-, di-, or tri-substituted, and optionally mono-, di-, or tri-substituted heteroaryl, said heteroaryl having from 1 to 3 rings, 5 to 7 ring members in each ring and, in at least one of said rings, from 1 to about 3 heteroatoms selected from the group consisting of N, O, and S.

R is oxygen or absent.

$Z_2$ is nitrogen or $CR_2$ and $Z_3$ is nitrogen or $CR_3$; with the proviso that $Z_2$ and $Z_3$ are not both nitrogen.

$R_1$, $R_2$, and $R_3$ are independently chosen from hydrogen, halogen, amino, cyano, nitro, optionally substituted alkyl, optionally substituted alkenyl, optionally substituted alkynyl, optionally substituted alkoxy, optionally substituted mono- or di-alkylamino, optionally substituted cycloalkyl, optionally substituted (cycloalkyl)alkyl, optionally substituted (cycloalkyl)oxy, optionally substituted (cycloalkyl) alkoxy, optionally substituted alkylthio, optionally substituted alkylsulfinyl, optionally substituted alkylsulfonyl, and optionally substituted mono- or dialkylcarboxamide; with the proviso that not all of $R_1$, $R_3$, and $R_4$ are hydrogen.

The invention particularly includes compounds and pharmaceutically acceptable salts of Formula I in which:

$Ar_1$ and $Ar_2$ are independently chosen from phenyl which is mono-, di-, or tri-substituted, and 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, and triazolyl, each of which is optionally mono-, di-, or tri-substituted.

Preferred diarylpyrazine, diarylpyridine, and diarylpyrimidine compounds and particularly preferred 2,5-diarylpyrazines of the invention exhibit good activity in standard in vitro receptor binding assays, specifically the assay as specified in Example 9, which follows and is defined below. Particularly preferred 2,5-diarylpyrazines of the invention have an $IC_{50}$ of about 1 micromolar or less, still more preferably an $IC_{50}$ of about 100 nanomolar or less even more preferably an $IC_{50}$ of about 10 nanomolar or less or even 1 nanomolar or less in such a defined standard in vitro CRF receptor binding assay as exemplified by Example 9 which follows.

DETAILED DESCRIPTION OF THE INVENTION

Chemical Description and Terminology

Prior to setting forth the invention in detail, it may be helpful to provide definitions of certain terms to be used herein. Compounds of the present invention are generally described using standard nomenclature. Certain compounds are described herein using a general formula that includes variables. Unless otherwise specified, each variable within such a formula is defined independently of other variables.

In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Compounds having a sterically congested biaryl, aryl-heteroaryl or bi-heteroaryl bond, generically referred to as biaryl bonds, include those compounds having two, three or four substitutents on the aryl or heteroaryl ring ortho to the biaryl bond. Such biary compourns may exist as isolable enantiotopic rotational isomers with all isomeric forms of the compounds being included in the present invention. Where a compound exists in various tautomeric forms, the invention is not limited to any one of the specific tautomers, but rather includes all tautomeric forms. In these situations, the single enantiomers, i.e., optically active forms, can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0–2 R*, then said group may optionally be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom is replaced with a selection from the indicated group, provided that the designated atom's normal valence is not exceeded, and that the substitution results in a stable compound. When a substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a tetrahydropyridone.

As indicated above, various substituents of Formula I and Formula IA are "optionally substituted". The phrase "optionally substituted" indicates that such groups may either be unsubstituted or substituted at one or more of any of the available positions, typically 1, 2, 3, or 4 positions, by one or more suitable groups such as those disclosed herein.

When substituents such as Ar, $R_1$, $R_2$, $R_3$, and $R_4$, are further substituted, they may be so substituted at one or more available positions, typically 1 to 3 or 4 positions, by one or more suitable groups such as those disclosed herein. Suitable groups that may be present on a "substituted" Ar or other group include e.g., halogen; cyano; hydroxyl; nitro; azido; alkanoyl (such as a $C_1$–$C_6$ alkanoyl group such as acyl or the like); carboxamido; alkyl groups (including cycloalkyl groups, having 1 to about 8 carbon atoms, preferably 1, 2, 3, 4, 5, or 6 carbon atoms); alkenyl and alkynyl groups (including groups having one or more unsaturated linkages and from 2 to about 8, preferably 2, 3, 4, 5 or 6, carbon atoms); alkoxy groups having one or more oxygen linkages and from 1 to about 8, preferably 1, 2, 3, 4, 5 or 6 carbon atoms; aryloxy such as phenoxy; alkylthio groups including those having one or more thioether linkages and from 1 to about 8 carbon atoms, preferably 1, 2, 3, 4, 5 or 6 carbon atoms; alkylsulfinyl groups including those having one or more sulfinyl linkages and from 1 to about 8 carbon atoms, preferably 1, 2, 3, 4, 5, or 6 carbon atoms; alkylsulfonyl groups including those having one or more sulfonyl linkages and from 1 to about 8 carbon atoms, preferably 1, 2, 3, 4, 5, or 6 carbon atoms; aminoalkyl groups including groups having one or more N atoms and from 1 to about 8, preferably 1, 2, 3, 4, 5 or 6, carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being a preferred arylalkyl group; arylalkoxy having 1 to 3 separate or fused rings and from 6 to about 18 ring carbon atoms, with O-benzyl being a preferred arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("–") that is not between two letters or symbols is used to indicate a point of attachment for a substituent. For example, —$CONH_2$ is attached through the carbon atom.

As used herein, "alkyl" is intended to include both branched and straight-chain saturated aliphatic hydrocarbon groups, having the specified number of carbon atoms. Thus, the term $C_1$–$C_6$ alkyl as used herein includes alkyl groups consisting of 1 to 6 carbon atoms. When $C_0$–$C_n$alkyl is used herein in conjunction with another group, for example, aryl$C_0$–$C_4$alkyl, the indicated group, in this case aryl, is either directly bound by a single covalent bond, or attached by an alkyl chain having the specified number of carbon atoms, in this case from 1 to 4 carbon atoms. Examples of alkyl include, but are not limited to, methyl, ethyl, n-propyl, i-propyl, n-butyl, s-butyl, t-butyl, n-pentyl, and s-pentyl. Preferred alkyl groups are $C_1$–$C_8$ and $C_1$–$C_6$ alkyl groups. Especially preferred alkyl groups are methyl, ethyl, propyl, butyl, and 3-pentyl. "Carbhydryl" is intended to include both branched and straight-chain hydrocarbon groups, which are saturated or unsaturated, having the specified number of carbon atoms.

"Alkenyl" is intended to include hydrocarbon chains of either a straight or branched configuration comprising one or more unsaturated carbon-carbon bonds, which may occur in any stable point along the chain, such as ethenyl and propenyl.

"Alkynyl" is intended to include hydrocarbon chains of either a straight or branched configuration comprising one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

As used herein, the term "mono- or di-alkylamino" includes secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, methyl-propyl-amino.

As used herein, the term "alkylsulfinyl" includes those groups having one or more sulfoxide (SO) linkage groups and typically from 1 to about 8 carbon atoms, more typically 1 to about 6 carbon atoms.

As used herein, the term "alkylsulfonyl" includes those groups having one or more sulfonyl ($SO_2$) linkage groups and typically from 1 to about 8 carbon atoms, more typically 1 to about 6 carbon atoms.

As used herein, the term "alkylthio" includes those groups having one or more thioether linkages and preferably from 1 to about 8 carbon atoms, more typically 1 to about 6 carbon atoms.

As used herein, the term "aryl" indicates aromatic groups containing only carbon in the aromatic ring. Such aromatic groups may be further substituted with carbon or non-carbon atoms or groups. Typical aryl groups contain 1 to 3 separate, fused, or pendant rings and from 6 to about 18 ring atoms, without heteroatoms as ring members. Specifically preferred aryl groups include phenyl, naphthyl, including 1-naphthyl and 2-naphthyl, and biphenyl.

As used herein, "carbocyclic group" is intended to mean any stable 3- to 7-membered monocyclic group, which may be saturated, partially unsaturated, or aromatic. In addition to those exemplified elsewhere herein, examples of such carbocycles include, but are not limited to, cyclopropyl, cyclobutyl, cyclopentyl, cyclohexyl, cycloheptyl, cyclohexenyl, and phenyl.

"Cycloalkyl" is intended to include saturated hydrocarbon ring groups, having the specified number of carbon atoms, usually from 3 to about 8 ring carbon atoms. Preferred cycloalkyl groups have from 3 to 7 ring carbon atoms. Examples of cycloalkyl groups include cyclopropyl, cyclobutyl, cyclopentyl, or cyclohexyl and bridged or caged saturated ring groups such as norbornane or adamantane and the like.

In the term "(cycloalkyl)alkyl", cycloalkyl and alkyl are as defined above, and the point of attachment is on the alkyl group. This term encompasses, but is not limited to, cyclopropylmethyl, cyclohexylmethyl, and cyclohexylmethyl. Likewise, in the term "(cycloalkyl)alkoxy", cycloalkyl and alkoxy are as define above, and the point of attachment in the oxygen of the alkoxy group. The term "cycloalkyloxy" indicates a cycloalkyl group, as defined above, attached through an oxygen bridge.

"Cycloalkenyl" is intended to include hydrocarbon ring groups, having the specified number of carbon atoms, usually from 3 to about 8 ring carbon atoms, which have at least one carbon-carbon double bond. Preferred cycloalkyl groups have from 3 to 7 ring carbon atoms. Examples of cycloalkenyl groups includecyclopentenyl, and cyclohexenyl groups.

"Haloalkyl" is intended to include both branched and straight-chain saturated aliphatic hydrocarbon groups having the specified number of carbon atoms, substituted with 1 or more halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

As used herein, the terms "heteroaryl" is intended to indicate a stable 5-to 7-membered monocyclic or bicyclic or 7- to 10-membered bicyclic heterocyclic ring which contains at least 1 aromatic ring that contains from 1 to 4 heteroatoms selected from N, O, and S, with remaining ring atoms being carbon. When the total number of S and O atoms in the heteroaryl group exceeds 1, that these heteroatoms are not adjacent to one another. It is preferred that the total number of S and O atoms in the heterocycle is not more than 1, 2, or 3, more typically 1 or 2. It is particularly preferred that the total number of S and O atoms in the aromatic heterocycle is not more than 1. Examples of heteroaryl groups include pyridyl, indolyl, pyrimidinyl, pyridizinyl, pyrazinyl, imidazolyl, oxazolyl, thienyl, thiazolyl, triazolyl, isoxazolyl, quinolinyl, pyrrolyl, pyrazolyl, and 5,6,7,8-tetrahydroisoquinoline.

The term "heterocycloalkyl" is used to indicate saturated cyclic groups contain from 1 to about 3 heteroatoms selected from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, and pyrrolidinyl groups.

As used herein, the term "heterocyclic group" is intended to include 3 to 7 membered saturated, partially unsaturated, or aromatic monocyclic groups having at least one atom selected from N, O or S. The remaining ring atoms are carbon. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. A nitrogen atom in the heterocycle may optionally be quaternized. It is preferred that the total number of heteroatoms in the heterocyclic groups is not more than 4 and that the total number of S and O atoms in the heterocyclic group is not more than 2, more preferably not more than 1.

Preferred heterocyclic groups include, but are not limited to, pyridinyl, pyrimidinyl, furanyl, thienyl, pyrrolyl, pyrazolyl, pyrrolidinyl, morpholinyl, piperidinyl, piperazinyl, and imidazolyl.

As used herein, "pharmaceutically acceptable salts" refer to derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0–4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences,* 17th ed., Mack Publishing Company, Easton, Pa., p. 1418 (1985).

"Prodrugs" are intended to include any compounds that become compounds of Formula I when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of Formula I.

The term "therapeutically effective amount" of a compound of this invention means an amount effective, when administered to a human or non-human patient, to provide a therapeutic benefit such as an amelioration of symptoms, e.g., an amount effective to antagonize the effects of pathogenic levels of CRF or to treat the symptoms of stress disorders, affective disorder, anxiety or depression.

CRF1 Receptor Ligands

The present invention is based, in part, on the discovery that small molecules having the general Formula I, shown above (as well as pharmaceutically acceptable salts and prodrugs thereof) act as antagonists and/or inverse agonists of CRF1 receptors.

In addition to compounds and pharmaceutically acceptable salts of Formula I set forth above, the invention provides certain compounds and pharmaceutically acceptable salts thereof, of Formula I, which will be referred to as compounds of Formula IA in which the variables R, $R_1$, $Ar_1$, $Z_2$, $Z_3$ and $Ar_2$ carry the following definitions:

R is oxygen or absent.

$Z_2$ is nitrogen or $CR_2$ and $Z_3$ is nitrogen or $CR_3$. $Z^2$ and $Z^3$ are not both nitrogen.

$Ar_1$ and $Ar_2$ are independently chosen from phenyl which is mono-, di-, or tri-substituted with $R_A$, and 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, and triazolyl, each of which is optionally mono-, di-, or tri-substituted with $R_A$.

$R_1$, $R_2$, and $R_3$ are independently selected from hydrogen, halogen, hydroxy, cyano, amino, nitro, $C_1$–$C_6$alkyl$_1$, $C_1$–$C_6$alkyl$_1$—O—, mono- or di-($C_1$–$C_6$alkyl$_1$)amino, $C_3$–$C_7$cycloalkyl$_2$($C_0$–$C_4$alkyl$_1$), $C_3$–$C_7$cycloalkenyl$_2$ ($C_0$–$C_4$alkyll$_1$), $C_3$–$C_7$cycloalkyl$_2$($C_0$–$C_4$alkyl$_1$)—O—, $C_3$–$C_7$cycloalkenyl$_2$($C_0$–$C_4$alkyl$_1$)—O—, halo$C_1$–$C_6$alkyl$_1$, halo$C_1$–$C_6$akyl$_1$—O—, and —S(O)$_n$($C_1$–$C_6$alkyl$_1$). Each alkyl$_1$ is independently straight or branched, contains 0 or 1 or more double or triple bonds, and is unsubstituted or substituted with one or more substituents independently chosen from halogen, hydroxy, oxo, cyano, $C_1$–$C_4$alkoxy, amino, and mono- or di-($C_1$–$C_4$alkyl)amino, and each $C_3$–$C_7$cycloalkyl$_2$ and $C_3$–$C_7$cycloalkenyl$_2$ is optionally substituted by one or more substituents independently chosen from halogen, hydroxy, oxo, cyano, $C_1$–$C_4$alkoxy, amino, and mono- or di-($C_1$–$C_4$)alkylamino. Not all of $R_1$, $R_2$, and $R_3$ are hydrogen.

$R_A$ is independently selected at each occurrence from halogen, cyano, nitro, halo($C_1$–$C_6$)alkyl, halo($C_1$–$C_6$) alkoxy, hydroxy, amino, $C_1$–$C_6$alkyl substituted with 0–2 $R_B$, $C_2$–$C_6$alkenyl substituted with 0–2 $R_B$, $C_2$–$C_6$alkynyl substituted with 0–2 $R_B$, $C_3$–$C_7$cycloalkyl substituted with 0–2 $R_B$, ($C_3$–$C_7$cycloalkyl)$C_1$–$C_4$alkyl substituted with 0–2 $R_B$, $C_1$–$C_6$alkoxy substituted with 0–2 $R_B$, —NH ($C_1$–$C_6$alkyl) substituted with 0–2 $R_B$, —N($C_1$–$C_6$alkyl) ($C_1$–$C_6$alkyl) where each $C_1$–$C_6$alkyl is independently substituted with 0–2 $R_B$, —XR$_C$, and Y.

$R_B$ is independently selected at each occurrence from halogen, hydroxy, cyano, amino, $C_1$–$C_4$alkyl, $C_1$–$C_4$alkoxy, mono- or di-($C_1$–$C_4$alkyl)amino, —S(O)$_n$(alkyl), halo ($C_1$–$C_4$)alkyl, halo($C_1$–$C_4$)alkoxy, —CO($C_1$–$C_4$alkyl), —CONH($C_1$–$C_4$alkyl), —CON($C_1$–$C_4$alkyl)($C_1$–$C_4$alkyl), —XR$_C$, and Y.

$R_C$ and $R_D$, are the same or different, and are independently selected at each occurrence from: hydrogen, and straight, branched, and cyclic alkyl groups, and (cycloalkyl) alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, mono- or di-($C_1$–$C_4$alkyl)amino, —NHC(=O)($C_1$–$C_6$alkyl), —N($C_1$–$C_6$alkyl)C(=O)($C_1$–$C_6$alkyl), —NHS(O)$_n$ ($C_1$–$C_6$alkyl), —S(O)$_n$($C_1$–$C_6$alkyl), —S(O)$_n$NH ($C_1$–$C_6$alkyl), —S(O)$_n$N($C_1$–$C_6$alkyl)($C_1$–$C_6$alkyl), and Z.

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$ NH—, —S(O)$_n$NR$_D$—, —OC(=S)S—, —NHC(=O)—, —NR$_D$C(=O)—, —NHS(O)$_n$—, and —NR$_D$S(O)$_n$—.

Y and Z are independently selected at each occurrence from: 3- to 7-membered carbocyclic or heterocyclic groups, which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, and —S(O)$_n$(alkyl), wherein said 3- to 7-memberered heterocyclic groups contain from 1 to 3 heteroatom(s) independently selected from N, O, and S, with remaining ring members being carbon.

At each occurrence n is independently selected from 0, 1, and 2.

In particular embodiments the invention provides compounds and pharmaceutically acceptable salts of Formula IA in which $Z_2$ is nitrogen and $Z_3$ is $CR_3$, i.e. compounds of Formula A.

The inventions also includes provides compounds and pharmaceutically acceptable salts of Formula IA in which $Z_2$ is $CR_2$ and $Z_3$ is $CR_3$, i.e. compounds of Formula B.

Further included in the invention are compounds and pharmaceutically acceptable salts of Formula IA in which $Z_2$ is $CR_2$ and $Z_3$ is nitrogen, i.e. compounds of Formula C.

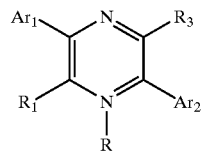

Formula A

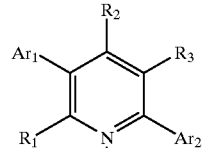

Formula B

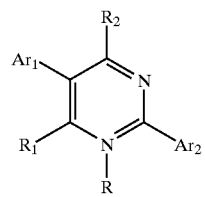

Formula C

The remaining variables of Formula A, Formula B, and Formula C, e.g., R, $R_1$, $R_2$, $R_3$, $Ar_1$, and $Ar_2$, carry the definitions set forth for compounds and salts of Formula IA.

Particular embodiments of the invention include compounds and pharmaceutically acceptable salts of Formula IA in which R is absent. $Ar_2$, in this particular embodiment, is phenyl or pyridyl, each of which is mono-, di-, or tri-substituted with $R_A$.

Another specific embodiment of the invention pertains to compounds and pharmaceutically acceptable salts of Formula IA in which R is absent.

$R_1$, $R_2$, and $R_3$, in this specific embodiment, are independently selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl) $C_0$–$C_3$alkoxy, vii) mono- or di-($C_1$–$C_3$alkyl)amino, viii)

$C_1$–$C_3$haloalkyl, and ix) $C_1$–$C_3$haloalkoxy wherein each of iii, iv, v, vi, and vii is unsubstituted or substituted by 1–3 groups independently chosen from hydroxy, amino, cyano, and halogen.

$Ar_2$, in this specific embodiment of the invention, is preferably phenyl or pyridyl, each of which is substituted with $R_A$ at at least 1 position ortho to the point of attachment of Ar in Formula I, and optionally substituted with up to 2 additional $R_A$ groups.

The invention further provides compounds and pharmaceutically acceptable salts of Formula IA in which R is absent.

$Ar_2$, in these further provided compounds and salts, is phenyl or pyridyl, each of which is substituted with $R_A$ at at least 1 position ortho to the point of attachment of Ar in Formula I, and optionally substituted with up to 2 additional $R_A$ groups.

$R_C$ and $R_D$, in these further provided compounds and salts, may be the same or different, are independently selected at each occurrence from straight, branched, or cyclic alkyl groups having from 1 to 8 carbon atoms, which alkyl groups may contain one or more double or triple bonds.

$R_1$, $R_2$, and $R_3$, in certain compounds and salts of these further provided compounds and salts, are independently selected from the group consisting of i) hydrogen, ii) halogen, iii) $C_1$–$C_3$alkyl, iv) $C_1$–$C_3$alkoxy, v) $(C_3$–$C_7$cycloalkyl)$C_0$–$C_3$alkyl, vi) $(C_3$–$C_7$cycloalkyl)$C_0$–$C_3$alkoxy, vii) mono- or di-$(C_1$–$C_3$alkyl)amino, viii) $C_1$–$C_3$haloalkyl, and ix) $C_1$–$C_3$haloalkoxy wherein each of iii, iv, v, vi, and vii is unsubstituted or substituted by 1–3 groups independently chosen from hydroxy, amino, cyano, and halogen.

In yet another particular embodiment the invention provides compounds and pharmaceutically acceptable salts of Formula A, Formula B, and Formula C, in which R is absent.

$Ar_1$, in this particular embodiment, is chosen from phenyl which is mono-, di-, or tri-substituted with $R_A$, and 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, and triazolyl, each of which is optionally mono-, di-, or tri-substituted with $R_A$.

$Ar_2$, in this particular embodiment, is phenyl or pyridyl, each of which is substituted at at least 1 position ortho to the point of attachment of Ar in Formula I, and optionally substituted with up to 2 additional $R_A$ groups.

In certain preferred compounds and salts of this particular embodiment:

$R_1$, $R_2$, $R_3$ are independently selected from hydrogen, cyano, amino, halogen, $C_1$–$C_6$alkyl, $C_1$–$C_6$alkoxy, $(C_3$–$C_7$cycloalkyl)$C_0$–$C_3$alkyl, $(C_3$–$C_7$cycloalkyl)$C_0$–$C_3$alkoxy, mono- or di-$(C_1$–$C_6$alkyl)amino, $C_1$–$C_6$haloalkyl, $C_1$–$C_6$haloalkoxy, and —$SO_n$($C_1$–$C_6$alkyl).

$R_A$ is independently selected at each occurrence from i) halogen, cyano, nitro, halo($C_1$–$C_6$)alkyl, halo($C_1$–$C_6$)alkoxy, hydroxy, amino, $C_1$–$C_6$alkyl, $C_2$–$C_6$alkenyl, $C_2$–$C_6$alkynyl, $C_3$–$C_7$cycloalkyl, $(C_3$–$C_7$cycloalkyl)$C_1$–$C_4$alkyl, $C_1$–$C_6$alkoxy, mono- or di-$(C_1$–$C_6$alkyl)amino, —CHO, and —C(=O)$CH_3$; ii) $C_1$–$C_6$alkoxy and $C_1$–$C_6$ alkyl which is unsubstituted or substituted with 1 or 2 groups independently selected from halogen, hydroxy, cyano, amino, oxo, $C_1$–$C_4$alkoxy, mono- or di-$(C_1$–$C_6$alkyl) amino, halo($C_1$–$C_4$)alkyl, halo($C_1$–$C_4$)alkoxy, $C_1$–$C_4$alkanoyl, morpholinyl, piperazinyl, piperidinyl, furanyl, and pyrrolidinyl, and iii)3- to 7-membered carbocyclic or heterocyclic groups which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-$(C_1$–$C_4$alkyl)amino; and n is 0, 1, or 2.

In certain more preferred compounds and salts of this particular embodiment, $R_1$ and $R_3$ are independently selected from the group consisting of hydrogen, halogen, $C_1$–$C_4$alkyl, $C_1$–$C_3$alkoxy, $(C_3$–$C_7$cycloalkyl)$C_0$–$C_3$alkyl, $(C_3$–$C_7$cycloalkyl)$C_0$–$C_3$alkoxy, mono- or di-$(C_1$–$C_3$alkyl) amino, $C_1$–$C_3$haloalkyl, and $C_1$–$C_3$haloalkoxy; and $Ar_1$ is selected from the group consisting of phenyl which is mono- di- or trisubstituted, and 1-naphthyl, 2-naphthyl, pyridyl, pyrimidinyl, pyrazolyl, imidazolyl, tetrazolyl, and pyrazinyl, each of which is optionally mono- di- or trisubstituted with $R_A$.

The invention further includes compounds and pharmaceutically acceptably salts of Formula II, Formula IV, and Formula VI.

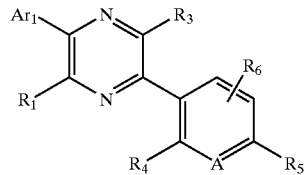

Formula II

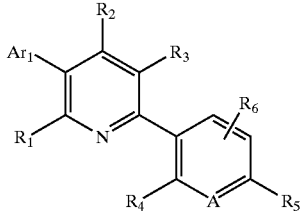

Formula IV

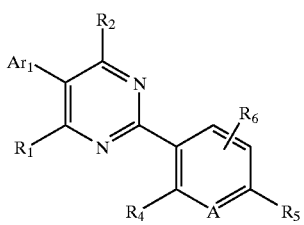

Formula VI

A is nitrogen or CH, in each of Formula II, Formula IV, and Formula VI.

$R_1$, $R_2$, and $R_3$ are independently chosen from hydrogen, halogen, methyl, ethyl, methoxy, ethoxy, trifluoromethyl, trifluoromethoxy, and methylamino;

$R_4$ and $R_5$, are independently chosen from halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-$(C_1$–$C_2$alkyl) amino;

$R_6$ is chosen from hydrogen, halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-$(C_1$–$C_2$alkyl)amino.

The invention further provides compounds and pharmaceutically acceptable salts of Formula III, Formula V, and Formula VII

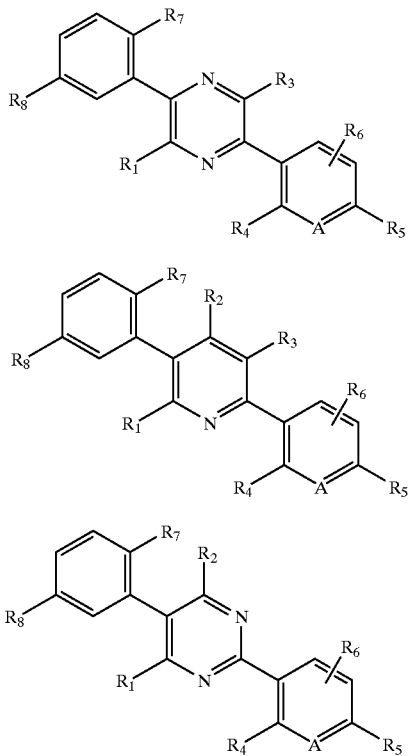

Formula III

Formula V

Formula VII

A is nitrogen or CH, in each of Formula III, Formula V, and Formula VII;

$R_1$, $R_2$, and $R_3$ are independently chosen from hydrogen, halogen, methyl, ethyl, methoxy, ethoxy, trifluoromethyl, trifluoromethoxy, and methylamino;

$R_4$ and $R_5$, are independently chosen from halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-($C_1$–$C_2$alkyl)amino;

$R_6$ is chosen from hydrogen, halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-($C_1$–$C_2$alkyl)amino;

$R^7$ and $R^8$ are independently chosen from methyl, ethyl, methoxy, ethoxy, trifluoromethyl and trifluoromethoxy and halogen.

Preferred substituents of the $Ar_1$ and $Ar_2$ groups, for compounds of Formula I, Formula IA and the subformulae thereof, including, for example, compounds of Formula A–C include chloro, methyl, methoxy, ethyl, ethoxy, trifluoromethoxy, difluoromethoxy, trifluoromethyl, difluoromethyl, 1-ethyl-propoxy, isopropoxy, isopropyl, and isopropyl amino.

Particularly preferred $Ar_1$ groups include 3,5-diethyl-pyrazol-1-yl, 3,5-dimethylpyrazol-1-yl, 1-(1-ethyl-propyl)-1H-imidazol-2-yl, 2-methoxy-5-fluorophenyl, 2,5-difluorophenyl, 2-methoxy-5-isopropyl, 2,5-dichlorophenyl, 2,5-dimethoxyphenyl, 2-methoxy-5-chlorophenyl, 2-methoxy-5-isopropyl, 2,5-dimethylphenyl, 2-methoxy-4-trifluoromethoxy, phenyl, o-tolyl, 2-trifluoromethylphenyl, m-tolyl, 3-trifluoromethylphenyl, 2,3-dimethylphenyl, 3,5-dimethylphenyl, 2,6-dimethylphenyl, 2,4,6-trimethylphenyl, 2,4-dimethoxyphenyl, 2-methoxy-5-chlorophenyl, 2-methoxy-5-isopropylphenyl, 2,3,5-trichlorophenyl, 3-methyl-4-fluorophenyl, 3-trifluoromethoxyphenyl, 3,5-bis(trifluoro-methyl)phenyl, 1-naphthyl, 2-naphthyl, 3H-imidazole-4-carboxylic acid, 5-propyl-tetrazol-1-yl, and (3H-imidazole-4-yl)-morpholin-4-yl-methanone.

Particularly preferred $Ar_2$ groups, include, but are not limited to, 2,4-dimethoxy phenyl, 2-methoxy-4-ethyl phenyl, 2-methyl-4-methoxy phenyl, 2-methoxy-4-trifluoromethoxy phenyl, 2,4-dichlorophenyl, 2-chloro-4-methoxy phenyl, 2-methoxy-4-isopropoxy phenyl, 2-chloro-4-isopropoxy phenyl, 2-methoxy-4-difluoromethoxy-phenyl, 2-methoxy-4-isopropyl phenyl, 2-difluoromethoxy-4-methoxy phenyl, 2-methoxy-4-trifluoromethoxy phenyl, 2-methoxy-4-ethoxy phenyl, 2-methoxy-4-trifluoromethyl phenyl, 2-trifluoromethoxy-4-methoxy phenyl, 2-methyl-4-isopropyl 3-pyridyl, 2-methoxy-4-isopropyl-3-pyridyl, 2-ethoxy-4-isopropyl 3-pyridyl, 2-ethyl-4-isopropyl 3-pyridyl, and 2-ethyl-4-isopropylamino phenyl.

Preferred compounds of Formula I exhibit an $IC_{50}$ value of 1 micromolar or less in a standard in vitro CRF receptor binding assay. More preferred compounds exhibit an $IC_{50}$ value of 100 nanomolar or less in a standard in vitro CRF receptor binding assay. Particularly preferred compounds of Formula I exhibit an $IC_{50}$ value of 10 nanomolar or less in a standard in vitro CRF receptor binding assay. A standard in vitro CRF1 receptor binding assay is disclosed in Example 9, below.

The invention further provides intermediates useful in the preparation of compounds of Formula I, Formula IA, any the particular embodiments thereof (e.g., Formula A–Formula C and Formula II–Formula VII), or any of the compounds of Formula I specifically disclosed herein. Intermediates useful in the synthesis of compounds in the invention are described in Schemes I–III below, and further illustrated in Examples 1–7. For example, useful intermediates provided by the invention include organometallic aryl compounds, e.g., Ar-[M], and aryl boronic acids useful for coupling to the pyridine core of Formula I.

The invention also provides pharmaceutical compositions comprising a compound, pharmaceutically acceptable salt, or prodrug of Formula I, Formula IA, any the particular embodiments thereof (e.g., Formula A–Formula C and Formula II–Formula VII), or any of the compounds of Formula I specifically disclosed herein, together with a pharmaceutically acceptable carrier or excipient. Pharmaceutically acceptable carriers suitable for use in a composition provided by the invention may be inert, or may modulate the bioavailability or stability of the active compound. Representative carriers include, for example, molecules such as albumin, polylysine, polyamidoamines, peptides, proteins, polystyrene, polyacrylamide, lipids, ceramide and biotin, solid support materials such as beads and microparticles comprising, for example, polyacetate, polyglycolate, poly(lactide-co-glycolide), polyacrylate, starch, cellulose or dextran. The pharmaceutical composition, may be prepared in a variety of forms, for example, as an injectable fluid, an aerosol, a cream, a gel, a pill, a capsule, a syrup, or a transdermal patch.

The invention also provides packages comprising a pharmaceutical composition as described immediately above in a container and instructions for using the composition to treat a patient suffering from anxiety, or instructions for using the composition to treat a patient suffering from stress, or instructions for using the composition to treat a patient suffering from depression, or instructions for using the composition to treat a patient suffering from irritable bowel syndrome or instructions for using the composition to treat a patient suffering from Crohn's disease.

The CRF binding compounds provided by this invention and labeled derivatives thereof are also useful as standards and reagents in determining the ability of other compounds (e.g., a potential pharmaceutical agent) to bind to the CRF receptor.

The invention provides a method for demonstrating the presence of CRF receptors (preferably CRF1 receptors) in a biological sample (e.g., a tissue section or homogenate), said method comprising contacting the biological sample with a labeled compound of Formula I under conditions that permit binding of the labeled compound to a CRF receptor and detecting the labeled compound in the biological sample. Unbound labeled compound is preferably at least partially removed from the biological sample prior to detecting the bound labeled compound in the sample.

For detection purposes the compound may be labeled, for example, with a fluorescent, isotopic, or radiolabel. Radiolabeled and isotopically labeled compounds of Formula I–VIII and A–C, which are also included in the invention, are identical to the compounds recited in Formulae I–VIII and A–C, with one or more atoms replaced by an atom having an atomic mass or mass number different from the most highly abundant isotope of that atom. Examples of isotopes that can be incorporated into compounds of Formula I in accordance with this aspect of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{19}$F, and $^{36}$Cl. Preparation of such radiolabeled compounds of Formula I is described below in Example 10. The labeled compound may be detected if radiolabeled, e.g., autoradiographically, and if otherwise isotopically labeled, e.g., by NMR. Labeled derivatives the CRF antagonist compounds of Formula I are also useful as radiotracers for positron emission tomography (PET) imaging or for single photon emission computerized tomography (SPECT).

The present invention also pertains to methods of inhibiting the binding of CRF to CRF receptors which methods involve contacting a solution containing a compound of Formula I with at least one cell (e.g., a neuronal cell) expressing CRF receptors (e.g., preferably CRF1 receptors), wherein the compound is present in the solution at a concentration sufficient to inhibit CRF binding to CRF receptors in vitro. This method includes inhibiting the binding of CRF to CRF receptors in vivo in an animal (e.g., preferably a human patient). The animal is given an amount of a compound of Formula I that results in a concentration in a relevant body fluid (e.g., blood, plasma, serum, CSF, interstitial fluid) of the animal, which concentration is at least sufficient to inhibit the binding of CRF to CRF receptors in vitro.

The present invention also pertains to methods of altering (i.e. increasing or decreasing) the CRF-stimulated activity of CRF receptors, which methods involve contacting a solution containing a compound Formula I with at least one cell (e.g., a neuronal cell) expressing CRF receptors (e.g., preferably CRF1 receptors), wherein the compound is present in the solution at a concentration sufficient to alter the CRF-stimulated signal transduction activity of CRF receptors in cells expressing CRF receptors (preferably cells expressing such receptors at levels above those found in naturally occurring CRF receptor-expressing cells) in vitro. This method includes altering the CRF-stimulated activity of CRF receptors in vivo in an animal (e.g., preferably a human patient). The animal is given an amount of a compound of Formula I that results in compound a concentration in a relevant body fluid (e.g., blood, plasma, serum, CSF, interstitial fluid) of the animal, which concentration is at least sufficient to alter the CRF-stimulated activity of CRF receptors in vitro.

In one embodiment, such methods are useful in treating physiological disorders associated with excess concentrations of CRF in a patient (e.g., in a body fluid of the patient). The amount of a compound that would be sufficient to inhibit the binding of a CRF to a CRF receptor or to alter the CRF-stimulated activity of CRF receptors may be readily determined via a CRF receptor binding assay (see Example 9), or from the EC50 of a CRF receptor functional assay. CRF receptors that may be used to determine in vitro binding are found in a variety of sources, for example in cells that autologously express CRF receptors, e.g. IMR32 cells, or in a cell expressing a CRF receptor as a result of the expression of an exogenous CRF receptor-encoding polynucleotide comprised by the cell.

Methods of Treatment

Compounds of Formula I are useful in treating a variety of conditions including affective disorders, anxiety disorders, stress disorders, eating disorders, digestive disorders, and drug addiction.

Affective disorders include all types of depression, bipolar disorder, cyclothymia, and dysthymia.

Anxiety disorders include generalized anxiety disorder, panic, phobias and obsessive-compulsive disorder.

Stress, including post-traumatic stress disorder, hemorrhagic stress, stress-induced psychotic episodes, psychosocial dwarfism, stress headaches, stress-induced immune systems disorders such as stress-induced fever, and stress-related sleep disorders.

Eating disorders include anorexia nervosa, bulimia nervosa, and obesity.

Digestive disorders include, but are not limited to, irritable bowel syndrome and Crohn's disease.

Modulators of the CRF receptors may also be useful in the treatment of a variety of neurological disorders including supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, disorders of pain perception such as fibromyalgia and epilepsy.

Additionally compounds of Formula I are useful as modulators of the CRF receptor in the treatment of a number of gastrointestinal, cardiovascular, hormonal, autoimmune and inflammatory conditions. Such conditions include ulcers, spastic colon, diarrhea, post operative ilius and colonic hypersensitivity associated with psychopathological disturbances or stress, hypertension, tachycardia, congestive heart failure, infertility, euthyroid sick syndrome, inflammatory conditions effected by rheumatoid arthritis and osteoarthritis, pain, asthma, psoriasis and allergies.

Compounds of Formula I are also useful as modulators of the CRF1 receptor in the treatment of animal disorders associated with aberrant CRF levels. These conditions include porcine stress syndrome, bovine shipping fever, equine paroxysmal fibrillation, and dysfunctions induced by confinement in chickens, sheering stress in sheep or human-animal interaction related stress in dogs, psychosocial dwarfism and hypoglycemia.

Typical subjects to which compounds of Formula I may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

Pharmaceutical Preparations

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrathecal injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired, other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl disteartate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable dilutent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most CNS disorders, a dosage regimen of 4 times daily or less is preferred. For the treatment of stress and depression a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of Formula I will have certain pharmacological properties. Such properties include, but are not limited to oral bioavailability, low toxicity, low serum protein binding and desirable in vitro and in vivo half-lifes. Penetration of the blood brain barrier for compounds used to treat CNS disorders is necessary, while low brain levels of compounds used to treat periphereal disorders are often preferred.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

As discussed above, preferred arylpyridines of Formula I exhibit activity in standard in vitro CRF receptor binding assays, specifically the assay as specified in Example 9, which follows. References herein to "standard in vitro receptor binding assay" are intended to refer to that protocol as defined in Example 9 which follows. Generally preferred compounds preferred arylpyridines of Formula I have an $IC_{50}$ of about 1 micromolar or less, still more preferably and $IC_{50}$ of about 100 nanomolar or less even more preferably an $IC_{50}$ of about 10 nanomolar or less or even 1 nanomolar or less in such a defined standard in vitro CRF receptor binding assay as exemplified by Example 9 which follows.

EXAMPLES

Preparation of Diarylpyrazine, Diarylpyridine, and Diarylpyrimidine Compounds The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. All references cited in the description of Schemes I, II, and III are hereby incorporated by references for their teaching regarding the synthesis of diaryl pyrazines, pyridines, and pyrimidines and intermediates useful in the preparation of such compounds. Preferred methods for the preparation of compounds of the present invention include, but are not limited to, those described in Schemes I, II, and III. Unless otherwise indicated, Silica gel is used for purification of reaction products by column chromatography. Those who are skilled in the art will recognize that the starting materials may be varied and additional steps employed to produce compounds encompassed by the present invention.

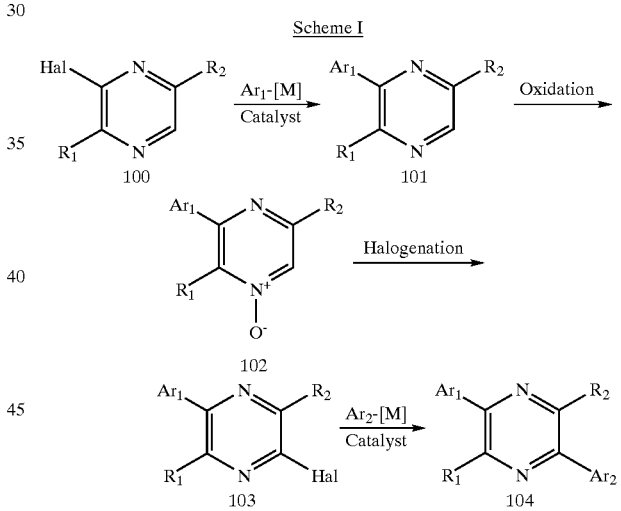

Scheme I

According to the method given in Scheme I, wherein $R_1$ and $R_2$ are as defined for Formula I and Hal represents a halogen atom, suitably chloride or bromide. Compounds of formula 100 can be obtained from commercial sources or can be prepared according to a known literature procedure (Ref: A. Ohta, et al. *Chem. Pharm. Bull.* 1979, 27(9), 2027). Conversion of halopyrazines 100 or 103 to a monoarylpyrazine 101 or diarylpyrazine 104, respectively, may be accomplished by a variety of transition metal-catalyzed coupling reactions with a metalloaryl reagent (Ar-[M]) via methods known in the art and described in the literature. More commonly employed reagent/catalyst pairs include aryl boronic acid/palladium(0) (Suzuki reaction; N. Miyaura and A. Suzuki, *Chem. Rev.* 1995, 95, 2457), aryl trialkylstannane/palladium(0) (Stille reaction; T. N. Mitchell, *Synthesis* 1992, 803), or arylzinc/palladium(0) and aryl Grignard/nickel(II). Palladium(0) represents a catalytic system made of a various combination of metal/ligand pairs which include, but are not limited to, tetrakis(triphenylphosphine)palladium(0), palladium(II) acetate/tri(o-tolyl)phosphine, tris(dibenzylideneacetone)dipalladium(0)/tri-tert-butylphosphine and dichloro[1,1'-bis(diphenylphosphine)ferrocene]palladium(0). Nickel(II) represents a nickel-containing catalyst such as [1,2-bis(diphenylphosphino)ethane]dichloronickel(II) and [1,3-bis(diphenylphosphino)propane]dichloronickel(II).

Scheme II

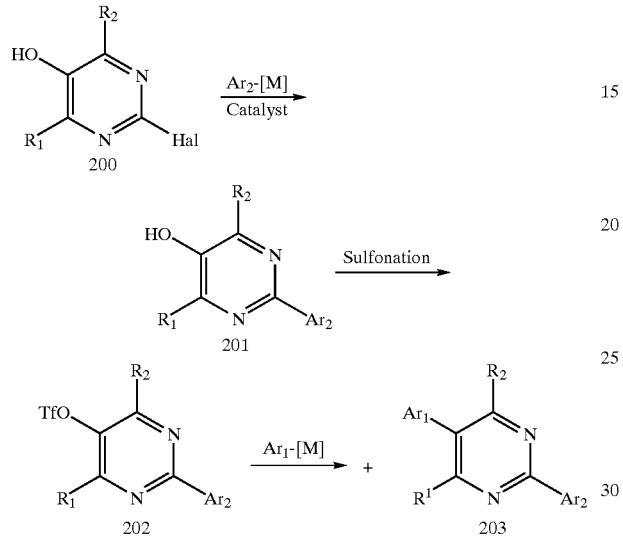

In Scheme II, the variable $R_1$, $R_2$, $Ar_1$, and $Ar_2$ carry the values set forth for compounds of Formula I. Hal represents a halogen atom, suitably chloride or bromide. Compounds of Formula 200 can be prepared from commercially available starting materials according to a known literature procedure (R. Dohmori, et al. *Chem. Pharm. Bull.* 1970, 18(9), 1908–1914). Conversion of halopyrimidines 200 to monoarylpyrimidines 201 may be accomplished by a transition metal-catalyzed coupling reaction with a metalloaryl reagent (Ar-[M]). More commonly employed reagent/catalyst pairs include aryl boronic acid/palladium(0) (Suzuki reaction; N. Miyaura and A. Suzuki, *Chem. Rev.* 1995, 95, 2457), aryl trialkylstannane/palladium(0) (Stille reaction; T. N. Mitchell, *Synthesis* 1992, 803), or arylzinc/palladium(0) and aryl Grignard/nickel(II). Palladium(0) represents a catalytic system made of a various combination of metal/ligand pair which includes, but not limited to, tetrakis(triphenylphosphine)palladium(0), palladium(II) acetate/tri(o-tolyl)phosphine, tris(dibenzylideneacetone)dipalladium(0)/tri-tert-butylphosphine and dichloro[1,1'-bis(diphenylphosphine)ferrocene]palladium(0). Nickel(II) represents a nickel-containing catalyst such as [1,2-bis(diphenylphosphino)ethane]dichloronickel(II) and [1,3-bis(diphenylphosphino)propane]dichloronickel(II). Hydroxypyrimidines 201 may be converted into trifluoromethanesulfonates (triflates) 202 with a sulfonating reagent such as but not limited to triflic anhydride or trifluoromethanesulfonyl chloride in the presence of bases such as but not limited to triethylamine or pyridine in inert solvents such as dichloromethane, at reaction temperatures between −78° C. and the boiling point of the solvent. Conversion of pyrimidines 202 into diarylpyrimidines 203 may be accomplished by a variety of transition metal-catalyzed coupling reaction with a metalloaryl reagent (Ar-[M]) as described above for the transformation of halopyrimidines 200 to 201.

Scheme III

Scheme for the synthesis of diarylpyridines:

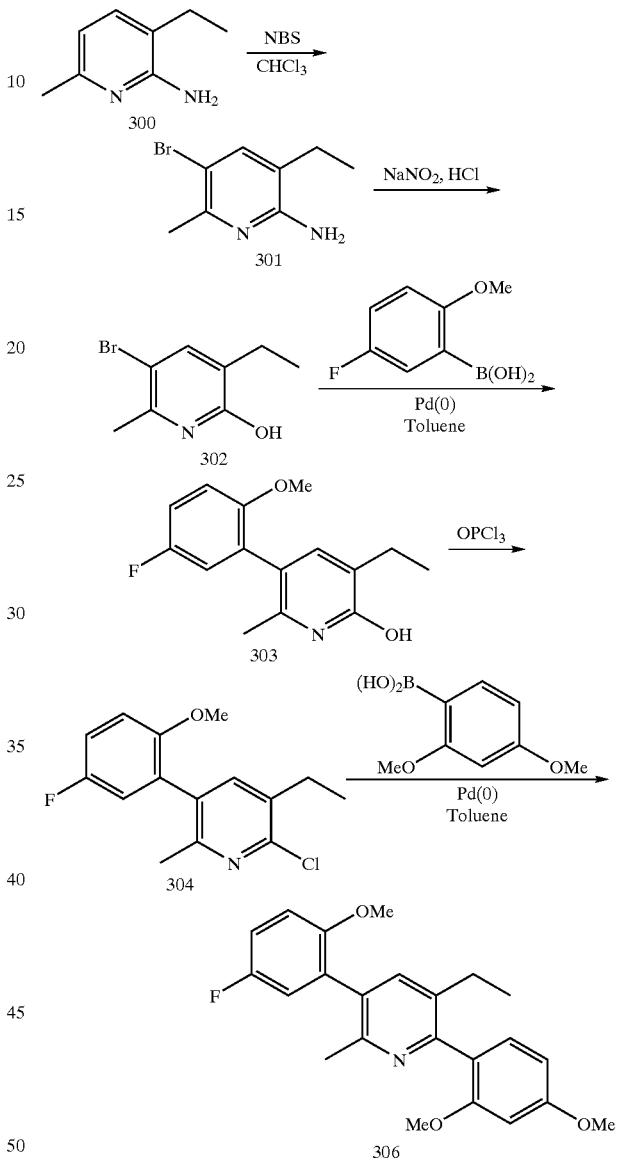

The pyridine 300 (starting material) is commercially available (Avocado Research Chemicals, Limited). Halogenation of 300 to bromopyridine 301 may be accomplished by a variety of methods known in the art, including treatment with N-chlorosuccinimide, bromine, N-bromosuccinimide, pyridinium tribromide, triphenylphosphine dibromide, iodine, and N-iodosuccinimide in solvents such as but not limited to dichloromethane, acetic acid, or methyl sulfoxide. Diazotization to pyridone 302 may be accomplished by a variety of reactions, including conversion to the diazonium salt by the action of sodium nitrite under acidic conditions, followed by decomposition of the diazonium salt to the hydroxypyridine, which tautomerizes to the corresponding pyridone 302. Transition metal-catalyzed (hetero)aryl-aryl coupling of X+2 can provide X+3 by reaction with a metalloaryl reagent (Ar-[M]), as previously stated for Scheme 1. More commonly employed reagent/catalyst pairs include aryl boronic acid/palladium(0) (Suzuki reaction; N. Miyaura and A. Suzuki, Chemical Reviews 1995, 95, 2457), aryl trialkylstannane/palladium(0) (Stille reaction; T. N. Mitchell, Synthesis 1992, 803), arylzinc/palladium(0) and aryl Grignard/nickel(II). Palladium(0) represents a catalytic system made of a various combination of metal/ligand pair which includes, but not limited to, tetrakis(triphenylphosphine)palladium(0), palladium(II) acetate/tri(o-tolyl)phosphine, tris(dibenzylideneacetone)dipalladium(0)/tri-tert-butylphosphine and dichloro[1,1'-bis(diphenylphosphine) ferrocene]palladium(0). Nickel(II) represents a nickel-containing catalyst such as [1,2-bis(diphenylphosphino) ethane]dichloronickel(II) and [1,3-bis(diphenylphosphino) propane]dichloronickel(II). Conversion of pyridone 303 to 2-chloropyridine 304 can be carried out by a variety of methods, including heating in the presence of $OPCl_3$, $PCl_3$, $PCl_5$, or $SOCl_2$. Coupling of chloropyridine 304 to the final product can again be carried out as previously stated for the transformation of 302 to 303.

The preparation of the compounds of the present invention is illustrated further by the following examples, which are not to be construed as limiting the invention in scope or spirit to the specific procedures and compounds described in them.

While not being bound by theory, a typical catalyst facilitates formation of the Ar—R product by the catalytic cycle depicted in Scheme IV below wherein an aryl halide added across a reduced metal center, $L_nM$, by oxidative addition to form a metal(aryl)(halide) complex, $L_nM(aryl)$ (halide). Transalkylation of the metal halide bond by the another organometalic aryl compound, Ar-[M'], results in the formation of a metal (aryl)(alkyl) complex and a metal salt byproduct (M'X). Reductive elimination of the product Ar—R through formation of the Ar—R bond regenerates the reduced metal center, $L_nM$, to reinitiate the catalytic cycle.

Scheme IV

Catalyst Precursor

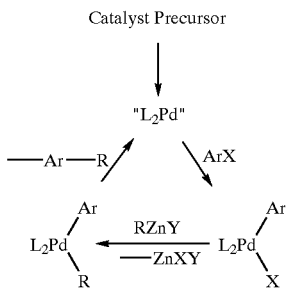

In general, ancillary ligands, $L_n$, are not particularly limited. In practice, typical ancillary ligands are frequently phosphines, particularly chelating bis(phosphines), and amines, particularly bipyridines. Particularly preferred ancillary ligands are chelating bis(phosphines) Preferred catalysts include palladium phosphine complexes which are either preformed or formed in situ from a palladium source and a phosphine. Preferred preformed catalysts include palladium (II) complexes $L_2PdCl_2$ and $L_2PdBr_2$ and palladium (0) complexes $L_2Pd(olefin)$ where $L_2$ is typically a chelating bis(phosphine) and olefin is an olefin which can coordinate to palladium such as ethylene, terminal and internal alkenes, styrene, stilbene, di(alkyl)malonate, norbornene, norbornadiene and the like. Preferred in situ catalysts "$L_2Pd$" are generated from a chelating bisphosphine ($L_2$) and a palladium(0) source such as $Pd_2$(dibenzylideneacetone)$_3$ and solvates thereof, palladium(0) phosphine complexes such as tetrakis(triphenylphosphine) palladium(0), bis(tricyclohexylphosphine)palladium(0) and other homoleptic palladium(0) phosphine complexes, and Pd(olefin)$_n$ complexes selected from Pd(ethylene)$_3$, Pd(norbornadiene)$_2$, Pd(1,5-cyclooctadiene)$_2$ and other stable isolable palladium olefin complexes. Other preferred in situ catalysts "$L_2Pd$" are generated from a chelating diphosphine ($L_2$), a palladium(II) source such as palladium acetate and a reductant such as excess organometallic aryl compound (Ar-[M]).

In other preferred embodiments, the palladium catalyst is a $L_2Pd$ complex which may comprise additional ligands bound to palladium, and L is phosphite or phosphite or $L_2$ taken in combination is chelating ligand selected from bis(phosphine), bis(phosphite), phosphine-phosphite or 2,2'-bipyridine derivative. More preferred palladium catalysts include those wherein $L_2$ is optionally substituted 1,1'-bis(diarylphosphino)-ferrocene, optionally substituted 2,2'-bis (diarylphosphino)-binaphthyl, optionally substituted 2,2'-bis (diarylphosphino)-biphenyl, optionally substituted α,ω-bis (diarylphosphino)-$C_{1-6}$alkylene, optionally substituted 1,2-bis(di$C_{1-8}$alkylphosphino)benzene, or 2,2'-bis (diarylphosphino)-diarylether.

In particularly preferred palladium catalysts suitable for use in the present invention include those wherein the ancillary ligand, $L_2$, is 1,1'-bis(diarylphosphino)-ferrocene, 2,2'-bis(diarylphosphino)-binaphthyl, or 2,2'-bis (diarylphosphino)-diphenylether; and aryl is phenyl, 2-tolyl, 3-tolyl, or 4-tolyl.

Paricularly preferred palladium catalysts include $L_2PdBr_2$, $L_2PdCl_2$, and mixtures of Pd(olefin)$_n$ and $L_2$, a chelating bis(phosphine), wherein olefin is selected from dibenzylidene acetone, norbornadiene, 1,5-cyclooctadiene, and ethylene such that 3 or 4 C=C bonds are coordinated to Pd; and $L_2$ is selected from 1,1'-bis(diarylphosphino)-ferrocene, 2,2'-bis(diarylphosphino)-binaphthyl, or 2,2'-bis (diarylphosphino)-diphenylether.

Preferred in situ catalysts prepared from a mixture of Pd(olefin)$_n$ and a chelating bis(phosphine) are generated by mixing the Pd(olefin)$_n$ and chelating bis(phosphine) at a molar ratio between about 1:1 and about 1:3 or more preferably between about 1:1 and about 1:1.5.

In preferred methods of the invention, the initial concentration of palladium is less than the initial concentration of the aryl halide component, e.g., the palladium complex is present in a catalytic or substoichiometric quantity. Typically, the palladium catalyst is less than about 25 mole %, 20 mole %, 15 mole %, 10 mole %, 5 mole %, 4 mole %, 2.5 mole %, 2 mole % or 1 mole % relative to the aryl halide (Ar—X) component. Particularly preferred palladium catalyst loadings are less than about 5 mole %, 2 mole % and 1 mole % relative to aryl halide.

Commercial reagents are used without further purification. Room or ambient temperature refers to 20 to 25° C. Concentration in vacuo implies the use of a rotary evaporator. TLC refers to thin layer chromatography. Proton nuclear magnetic resonance ($^1$H NMR) spectral data are obtained at 300 or 400 MHz. Chemical shifts are referred to TMS=0 ppm. Mass spectral data are obtained either by CI or APCI methods.

Example 1

Preparation of 2-(2,4-Dimethoxy-phenyl)-5-(2-methoxy-4-trifluoromethoxy-phenyl)-3,6-dimethyl-pyrazine Step 1. Preparation of 3-(2,4-dimethoxy-phenyl)-2,5-dimethyl-pyrazine A mixture of 3-chloro-2,5-dimethyl-pyrazine (283 mg, 2.0 mmol), 2,4-dimethoxyphenylboronic acid (455 mg, 2.5 mmol), tetrakis(triphenylphosphine)palladium (0) (115 mg, 5 mol %) in DME (12 mL) and sodium carbonate (1M in water, 4 mL) is heated at 75° C. (oil bath temperature) in a pressure tube for 14 hours. The reaction is cooled to room temperature, diluted with ethyl acetate, and washed with NaOH (2M) and then brine (2×50 mL). The solvents are dried (sodium sulfate) and removed under reduced pressure. Flash chromatography of the crude product (25% ethyl acetate in hexanes) yields 3-(2,4-dimethoxy-phenyl)-2,5-dimethyl-pyrazine as an oil MS: 245.

Step 2. Preparation of 3-(2,4-Dimethoxy-phenyl)-2,5-dimethyl-pyrazine 1-oxide

The product from step 1 (458 mg, 1.88 mmol) is dissolved in dichloromethane (30 mL) at room temperature, and 3-chloroperoxybenzoic acid (70%, 700 mg, 2.82 mmol) is added as a solid. The resulting solution is stirred at room temperature for 6 hours. The reaction is diluted with sodium carbonate solution (40 mL), the organic phase washed with brine, dried (sodium sulfate) and the solvents removed under reduced pressure to yield 3-(2,4-dimethoxy-phenyl)-2,5-dimethyl-pyrazine 1-oxide MS: 260.

Step 3. Preparation of 2-Chloro-5-(2,4-dimethoxy-phenyl)-3,6-dimethyl-pyrazine

The product from step 2 (444 mg) is dissolved in POCl$_3$ (1 mL) and DMF (N,N-dimethylformamide, 15 mL), and the resulting solution is stirred at 60° C. for 5 hours. The reaction mixture is cooled, and the volatiles removed under reduced pressure. Flash chromatography (30% ethyl acetate in hexanes) affords 2-chloro-5-(2,4-dimethoxy-phenyl)-3,6-dimethyl-pyrazine as a clear oil. MS: 279.

Step 4. Preparation of 2-(2,4-Dimethoxy-phenyl)-5-(2-methoxy-4-trifluoromethoxyphenyl)-3,6-dimethyl-pyrazine The product from step 3 (20 mg, 0.07 mmol), 2-methoxy-4-trifluoromethoxyphenylboronic acid (48 mg), tetrakis(triphenylphosphine)palladium(0) (12 mg), DME (0.8 mL) and sodium carbonate (1M, 0.2 mL) are combined in a pressure tube and heated at 80° C. (oil bath temperature) for 16 hours. After cooling to room temperature, the upper layer is loaded onto a preparative thin layer chromatography plate and the desired product obtained after elution with 20% ethyl acetate in hexanes. MS: 435. NMR (400 MHz, CDCl$_3$): 2.39(s, 3H), 2.44 (s, 3H), 3.81 (s, 3H), 3.83 (s, 3H), 3.78 (s, 3H), 6.56 (dd, 1H), 6.63 (dd, 1H), 6.84 (b, 1H), 6.97 (m, 1H), 7.30 (d, 1H), 7.39 (d, 1H).

Example 2

Preparation of 2-(2,4-Dimethoxy-phenyl)-5-(2,5-dimethyl-phenyl)-3,6-diethyl-pyrazine Step 1. Preparation of 3-(2,4-Dimethoxy-phenyl)-2,5-diethyl-pyrazine A mixture of 3-chloro-2,5-diethyl-pyrazine (2.83 g, 16.6 mmol) 2,4-dimethoxyphenylboronic acid (3.64 g, 20.0 mmol), tetrakis(triphenylphosphine)palladium (0) (84 mg, 0.7 mmol) in DME (100 mL) and sodium carbonate (1M in water, 30 mL) are heated at 75° C. (oil bath temperature) in a pressure tube for 14 hours. The reaction is cooled to room temperature, diluted with ethyl acetate, and washed with NaOH (2M) and then brine (2×50 mL). The solvents are dried (sodium sulfate) and removed under reduced pressure. Flash chromatography of the crude product (20% ethyl acetate in hexanes) yields 3-(2,4-dimethoxy-phenyl)-2,5-diethyl-pyrazine as an oil MS: 273.

Step 2. Preparation of 3-(2,4-Dimethoxy-phenyl)-2,5-diethyl-pyrazine 1-oxide

The product from step 1 (3.24 g, 11.9 mmol) is dissolved in dichloromethane (150 mL) at room temperature, and solid 3-chloroperoxybenzoic acid (4.46 g, 18 g) is added. The resulting solution is stirred overnight at room temperature. The reaction mixture is diluted with sodium carbonate solution (100 mL), the organic phase washed with brine, dried (sodium sulfate), and the solvents removed under reduced pressure to yield 3-(2,4-dimethoxy-phenyl)-2,5-diethyl-pyrazine 1-oxide MS: 288.

Step 3. Preparation of 2-Chloro-5-(2,4-dimethoxy-phenyl)-3,6-diethyl-pyrazine

The product from step 2 (3.3 g) is dissolved in POCl$_3$ (25 mL) and the resulting solution stirred at 60° C. for 6 hours. The reaction mixture is cooled, and the volatiles are removed under reduced pressure. Flash chromatography (1–4% ethyl acetate in hexanes) affords 2-chloro-5-(2,4-dimethoxy-phenyl)-3,6-diethyl-pyrazine as a clear oil. MS: 307. H-1 NMR (400 MHz, CDCl$_3$): 1.16 (t, 3H), 1.31 (t, 3H), 2.60 (q, 2H), 3.00 (q, 2H), 3.75 (s, 3H), 3.76 (s, 3H), 6.53 (d, 1H), 6.59 (dd, 1H), 7.19 (d, 1H).

Step 4. Preparation of 2-(2,4-Dimethoxy-phenyl)-5-(2,5-dimethyl-phenyl)-3,6-diethyl-pyrazine The product from step 3 (90 mg, 0.3 mmol), 2,5-dimethylphenylboronic acid (105 g, 1 mmol), tetrakis(triphenylphosphine)palladium(0) (50 mg), toluene (4 mL) and potassium carbonate (2M, 2 mL) were combined in a pressure tube and heated at 80° C. (oil bath temperature) for 16 hours. After cooling to room temperature, the upper layer is loaded onto a preparative thin layer chromatography plate and the desired product is obtained after elution with 20% ethyl acetate in hexanes. MS: 377. H-1 NMR (400 MHz, CDCl$_3$): 1.13 (t, 3H), 1.14 (t, 3H), 2.06 (s, 3H), 2.34 (s, 3H), 2.65 (m, 4H), 3.78 (s, 3H), 3.86 (s, 3H), 6.56 (d, 1H), 6.62 (dd, 1H), 7.1–7.2 (m, 3H), 7.31 (d, 1H).

Example 3

Preparation of 2-(2,4-Dimethoxy-phenyl)-3,6-diethyl-5-(5-fluoro-2-methoxy-phenyl)-pyrazine

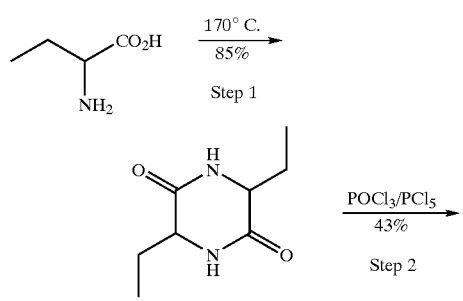

-continued

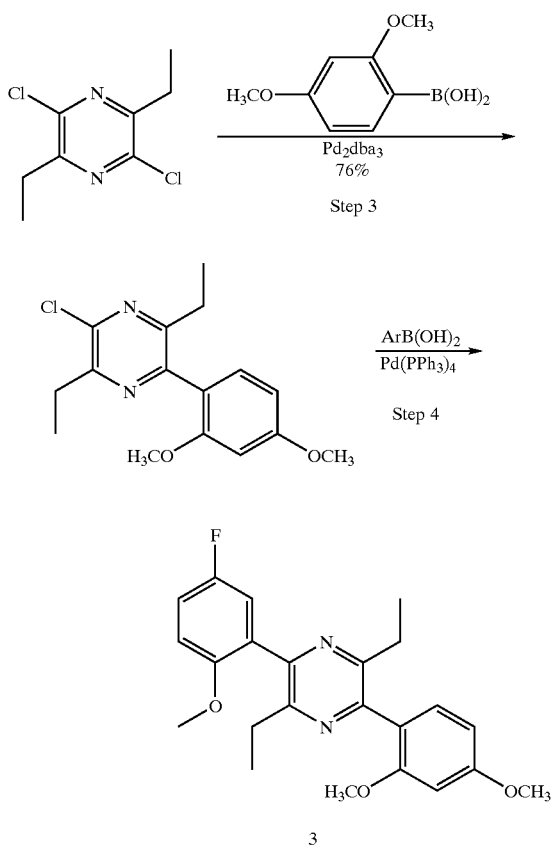

Step 1. Preparation of 3,6-Diethyl-piperazine-2,5-dione

D,L-2-Aminobutyric acid (20 g) is heated to gentle reflux in ethylene glycol (100 ml) for 20 hours, then cooled to room temperature, and poured into H₂O. The resulting precipitate is collected by filtration, washed with H₂O, and dried to give 3,6-Diethyl-piperazine-2,5-dione as a white solid. MS: 171.1 (M+1).

Step 2. Preparation of 2,5-Dichloro-3,6-diethyl-pyrazine

A mixture of 3,6-diethyl-piperazine-2,5-dione (30 g), PCl₅ (30 g) and POCl₃ (100 ml) is sealed and heated to 145° C. for 2.5 hours. After cooling to room temperature, the mixture is poured into ice, and extracted with Et₂O. The combined extracts are washed with H₂O, saturated NaHCO₃, and brine, dried, filtered and concentrated to give a yellow liquid. This liquid is purified by column chromatography (5% EtOAc in hexane) to give 2,5-dichloro-3,6-diethyl-pyrazine as a colorless liquid. MS: 204.9, 206.9, 208.9 (M+1). ¹H NMR (CDCl₃): δ 1.30 (t, 6H), 2.91 (q, 4H).

Step 3. Preparation of 2-Chloro-5-(2,4-dimethoxy-phenyl)-3,6-diethyl-pyrazine

PPh₃ (160 mg) is added to a solution of Pd₂ dba₃ (69 mg) in DME (15 ml) at room temperature, followed by the addition of 2,5-dichloro-3,6-diethyl-pyrazine (615 mg, 3 mmol), 2,4-dimethoxypghenylboronic acid (573 mg, 3.1 mmol) and Na₂CO₃ (1M, 6 ml). The resulting mixture is heated to 70° C. for 5 hours, and then cooled to room temperature. The reaction mixture is diluted with 50% EtOAc in hexane, washed with water and brine, dried, filtered and evaporated. The crude is purified by chromatography (eluted with 6% EtOAc in hexane) to give 2-chloro-5-(2,4-dimethoxy-phenyl)-3,6-diethyl-pyrazine as a light yellow oil. MS: 307.3, 309.3 (M+1). ¹H NMR (CDCl₃): δ 1.16 (t, 3H), 1.32 (t, 3H), 2.61 (q, 2H), 2.98 (q, 2H), 3.78 (s, 3H), 3.85 (s, 3H), 6.54 (d, 1H), 6.60 (dd, 1H), 7.20 (d, 1H).

Step 4. Preparation of 2-(2,4-Dimethoxy-phenyl)-3,6-diethyl-5-(5-fluoro-2-methoxy-phenyl)-pyrazine Pd(PPh₃)₄ (8 mg) is added to a solution of 2-chloro-5-(2,4-dimethoxy-phenyl)-3,6-diethyl-pyrazine (70 mg) in DME (2 ml) at room temperature, followed by 2-methoxy-5-fluorophenylboronic acid (45 mg) and Na₂CO₃ (1M, 0.5 ml). The resulting mixture is heated to 90° C. for 20 hours, then cooled to room temperature. The reaction mixture is diluted with 50% EtOAc in hexane and washed with water and brine, dried, filtered and evaporated. The crude is purified by chromatography (eluted with 15% EtOAc in hexane) to give 2-(2,4-Dimethoxy-phenyl)-3,6-diethyl-5-(5-fluoro-2-methoxy-phenyl)-pyrazine compound 3. MS: 397.3 (M+1).

Example 4

Preparation of 3-(3,5-Diethyl-pyrazol-1-yl)-2-methoxy-6-(2-methoxy-4-trifluoromethoxy-phenyl)-5-methyl-pyridine

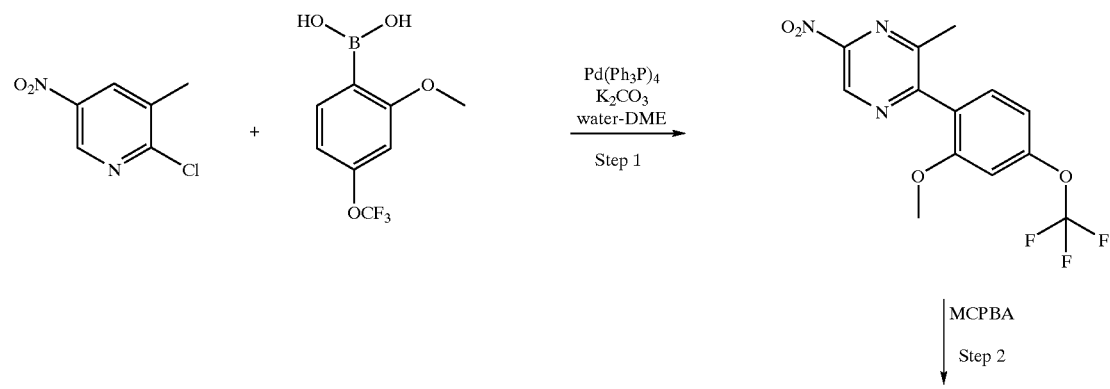

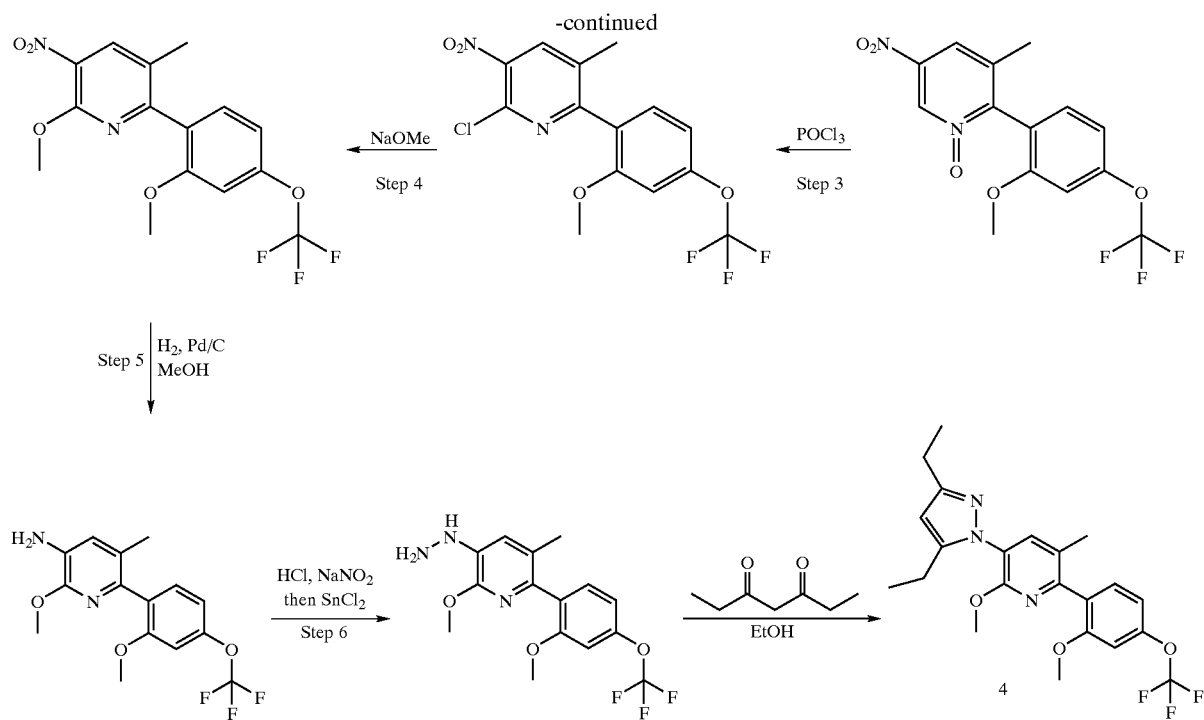

Step 1. Preparation of 2-Chloro-2-(2-methoxy-4-trifluoromethoxy-phenyl)-3-methyl-5-nitro-pyridine 2-methoxy-4-trifluoromethoxybenzene boronic acid (72 g, 0.31 mol), $K_2CO_3$ (80.16 g, 0.58 mol) and water (100 ml) are added to a solution of 2-chloro-3-methyl-5-nitro-pyridine (50 g, 0.29 mol) in DME (500 ml) at room temperature. $Pd(Ph_3P)_4$ (3.35 g, 2.9 mmol) is added and the mixture is stirred at 85° C. for 19 hours. 500 ml of water is added and the mixture is extracted with EtOAc. The combined extracts are washed with brine and dried over $Na_2SO_4$. After removal of the solvent under reduced pressure, the residue is purified by flash column chromatography (hexane/EtOAc 9:1) to obtain 2-(2-methoxy-4-trifluoromethoxy-phenyl)-3-methyl-5-nitro-pyridine. Rf (hexane/EtOAc=9:1)=0.41.

Step 2. 2-(2-methoxy-4-trifluoromethoxy-phenyl)-3-methyl-5-nitro-pyridine 1-oxide MCPBA (78.26 g, 0.349 mol) is added to a solution of 2-(2-methoxy-4-trifluoromethoxy-phenyl)-3-methyl-5-nitro-pyridine (95.6 g, 0.291 mol) in $CH_2Cl_2$ (500 ml) at room temperature. The mixture is stirred at room temperature for 3 hours. (1.2 L) and hexane (300 ml) and the mixture is washed with saturated aqueous $Na_2CO_3$ and brine. After drying over $Na_2SO_4$, the solvent is removed under reduced pressure to give 2-(2methoxy-4-trifluoromethoxy-phenyl)-3-methyl-5-nitro-pyridine 1-oxide as yellow solid. Rf (hexane/EtOAc=1:1)=0.40.

Step 3. 2-chloro-6-(2-methoxy-4-trifluoromethoxy-phenyl)-5-methyl-3-nitro-pyridine $POCl_3$ (500 ml) is added to 2-(2-methoxy-4-trifluoromethoxy-phenyl)-3-methyl-5-nitro-pyridine 1-oxide (97 g, 0.3 mol) at room temperature and the mixture is stirred at 75° C. for 2 hours. The mixture is concentrated under reduced pressure. Aqueous saturated $Na_2CO_3$ is added to the residue and the mixture is extracted with EtOAc. The combined extracts are washed with brine and dried over $Na_2SO_4$. The solvent is removed under reduced pressure. The residue is purified by flash column chromatography (hexane/EtOAc 10:1) to obtain 2-chloro-6-(2-methoxy-4-trifluoromethoxy-phenyl)-5-methyl-3-nitro-pyridine. Rf (hexane/EtOAc=9:1)=0.35.

Step 4.

A solution of sodium methoxide in MeOH (14 ml, 25%, 60.7 mmol) is added to a solution of 2-chloro-6-(2-methoxy-4-trifluoromethoxy-phenyl)-5-methyl-3-nitro-pyridine (20 g, 55.14 mmol) in MeOH (170 ml) at room temperature. The mixture is refluxed for 8 hours. Additional sodium methoxide in MeOH (14 ml, 25%, 60.7 mmol) is added and refluxed for 15 hours. After cooling to room temperature, the mixture is concentrated under reduced pressure. Water (300 ml) is added to the concentrated mixture and the mixture is extracted with EtOAc. The combined extracts are washed with brine and dried over $Na_2SO_4$. The solvent is removed under reduced pressure and the residue is purified by flash column chromatography (hexane/EtOAc 20:1) to give 2-methoxy-6-(2-methoxy-4-trifluoromethoxy-phenyl)-5-methyl-3-nitro-pyridine as white solid. Rf (hexane/EtOAc=9:1)=0.32.

Step 5. Preparation of 2-methoxy-6-(2-methoxy-4-trifluoromethoxy-phenyl)-5-methyl-pyridin-3-ylamine Pd/C (10%, 1.6 g) is added to a solution of 2-methoxy-6-(2-methoxy-4-trifluoromethoxy-phenyl)-5-methyl-3-nitro-pyridine (16.35 g, 45.635 mmol) in MeOH (450 ml) at room temperature. The suspension is stirred under hydrogen at room temperature for 5 hours. The catalyst is removed by filtration and the filtrate is concentrated under reduced pressure to give 2-methoxy-6-(2-methoxy-4-trifluoromethoxy-phenyl)-5-methyl-pyridin-3-ylamine as a gum. Rf (hexane/EtOAc=9:1)=0.18.

Step 6.

A solution of $NaNO_2$ (0.555 g, 8.04 mmol) in water (3 ml) is added to a stirred solution of 2-methoxy-6-(2-methoxy-4-trifluoromethoxy-phenyl)-5-methyl-pyridin-3-ylamine (2 g, 6.1 mmol) in concentrated HCl (3 ml), water (3 ml) and acetic acid (8 ml) below 0° C. over 20 minutes. The mixture is added to a stirred solution of $SnCl_2 \cdot 2H_2O$ (3.53 g, 15.7 mmol) in 4N HCl (9 ml) at 0° C. over 15 minutes. The mixture is stirred at 0° C. for 20 minutes and at room temperature for 30 minutes. The mixture is basified by NaOH solution at 0° C. and extracted with EtOAc. The combined extracts are dried over $Na_2SO_4$ and concentrated under reduced pressure to give [2-methoxy-6-(2-methoxy-4-trifluoromethoxy-phenyl)-5-methyl-pyridin-3-yl]-hydrazine. Rf (hexane/EtOAc=1:1)=0.24.

Step 7. Preparation of 3-(3,5-Diethyl-pyrazol-1-yl)-2-methoxy-6-(2-methoxy-4-trifluoromethoxy-phenyl)-5-methyl-pyridine 3,5-heptane dione (0.32 ml, 2.33 mmol) is added to a solution of [2-methoxy-6-(2-methoxy-4-trifluoromethoxy-phenyl)-5-methyl-pyridin-3-yl]-hydrazine (0.8 g, 2.33 mmol) in EtOH (15 ml) at room temperature. The mixture is refluxed for 15 hours. The solvent is removed under reduced pressure and the residue is purified by flash column chromatography to obtain 3-(3,5-Diethyl-pyrazol-1-yl)-2-methoxy-6-(2-methoxy-4-trifluoromethoxy-phenyl)-5-methyl-pyridine (Compound 4). Rf(hexane/EtOAc=9:1)=0.18, MS m/z 436.4 (M+H).

Example 5

Preparation of 2-Methoxy-6-(2-methoxy-4-trifluoromethoxy-phenyl)-5-methyl-3-(5-propyl-tetrazol-1-yl)-pyridine

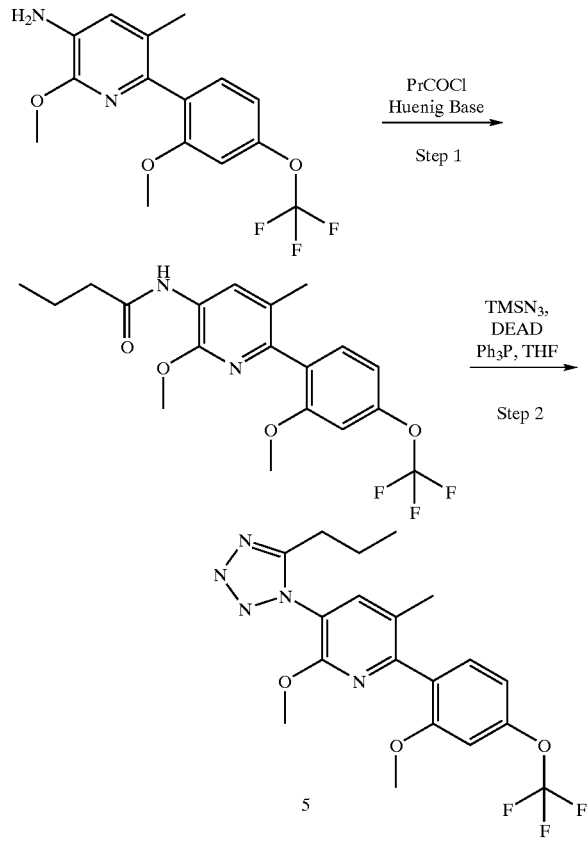

Step 1. Preparation of N-[2-methoxy-6-(2-methoxy-4-trifluoromethoxy-phenyl)-5-methyl-pyridin-3-yl]-butyramide Butyryl chloride (0.174 ml, 1.675 mmol) is added to a solution of 2-methoxy-6-(2-methoxy-4-trifluoromethoxy-phenyl)-5-methyl-pyridin-3-ylamine (0.5 g, 1.523 mmol) and diisopropylethylamine (0.32 ml, 1.83 mmol) in $CH_2Cl_2$ (10 ml) at room temperature. The mixture is stirred at room temperature for 30 minutes. EtOAc (50 ml) is added and the mixture is washed with 1 N NaOH and brine. After drying over $Na_2SO_4$, the solvent is removed under reduced pressure. The residue is purified by flash column chromatography (hexane/EtOAc=4:1) to give N-[2-methoxy-6-(2-methoxy-4-trifluoromethoxy-phenyl)-5-methyl-pyridin-3-yl]-butyramide. Rf (hexane/EtOAc=4:1)=0.46.

Step 2. Preparation of 2-Methoxy-6-(2-methoxy-4-trifluoromethoxy-phenyl)-5-methyl-3-(5-propyl-tetrazol-1-yl)-pyridine DEAD (0.12 ml, 0.75 mmol), triphenylphosphine (0.2 g, 0.75 mmol) and $TMSN_3$ (0.1 ml, 0.75 mmol) is added to a solution of N-[2-methoxy-6-(2-methoxy-4-trifluoromethoxy-phenyl)-5-methyl-pyridin-3-yl]-butyramide (0.15 g, 0.377 mmol) in THF (4 ml) is added at room temperature. The mixture is stirred at room temperature for 15 hours and concentrated under reduced pressure. The residue is purified by flash column chromatography (hexane/EtOAc=4:1) to give compound 5. Rf (hexane/EtOAc=4:1)=0.18, MS m/z 424.3 (M+H).

Example 6

Preparation of {3-[2-Methoxy-6-(2-methoxy-4-trifluoromethoxy-phenyl)-5-methyl-pyridin-3-yl]-3H-imidazole-4-yl}-morpholin-4-yl-methanone Step 1. Preparation of Methoxy-[2-methoxy-6-(2-methoxy-4-trifluoromethoxy-phenyl)-5-methyl-pyridin-3-ylamino]-acetic acid ethyl ester

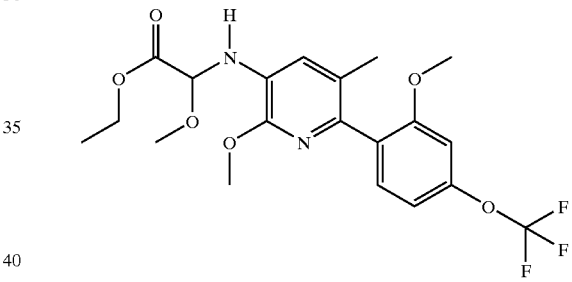

A solution of 2 methoxy-6-(2-methoxy-4-trifluoromethoxy-phenyl)-5-methyl-pyridin-3-yl-amine (5.0 g, 15.2 mmol) and ethyl glyoxylate (9.0 mL, 45 mmol) in MeOH (150 mL) is heated to reflux overnight. After cooling the mixture is concentrated under reduced pressure to give methoxy-[2-methoxy-6-(2-methoxy-4-trifluoromethoxy-phenyl)-5-methyl-pyridin-3-ylamino]-acetic acid ethyl ester as a oil which is used without further purification. TLC $R_f$ 0.35 (elution with 10% ethyl acetate-hexane)

Step 2. Preparation of 3-[6-(2-Hydroxy-4-trifluoromethoxy-phenyl)-2-methoxy-5-methyl-pyridin-3-yl-3H-imdazaole-4-carboxylic acid ethyl ester

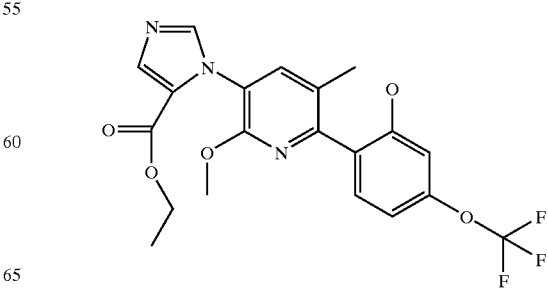

A solution of methoxy-[2-methoxy-6-(2-methoxy-4-trifluoromethoxy-phenyl)-5-methyl-pyridin-3-ylamino]-acetic acid ethyl ester (6.8 g, 15.3 mmol), and potassium carbonate (8.5, 61.2 mmol) in ethanol (150 mL) is treated with p-(tolylsulfonyl)methyl isocyanide (7.5 g, 38.25 mmol). The solution is heated to reflux for 2 hours. After cooling to room temperature, the solution is diluted with ethyl acetate (200 mL) and washed successively with 10% HCl (200 mL) and saturated aqueous NaCl (200 mL). The organic layer is separated, dried over $Na_2SO_4$, filtered and concentrated. Purification by flash column chromatography (2% methanol-methylene chloride) gives [2-methoxy-6-(2-methoxy-4-trifluoromethoxy-phenyl)-5-methyl-pyridin-3-yl]-3H-imidazole-4-carboxylic acid ethyl ester as a yellow oil TLC $R_f$ 0.40 (elution with 5% methanol-methylene chloride).

Step 3. Preparation of 3-[2-methoxy-6-(2-methoxy-4-trifluoromethoxy-phenyl)-5-methyl-pyridin-3-yl]-3H-imidazole-4-carboxylic acid

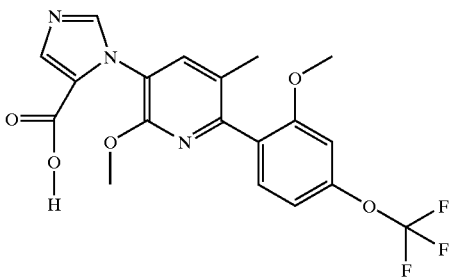

A solution of methanol [2-methoxy-6-(2-methoxy-4-trifluoromethoxy-phenyl)-5-methyl-pyridin-3-yl]-3H-imidazole-4-carboxylic acid ethyl ester (1 g, 4.23 mmol) and 1N NaOH (20 ml) in ethanol (30 mL)) is heated at 60° C. for 2 hours. The reaction mixture is diluted with EtOAc (30 mL) and washed with aqueous 1 N HCl (50 mL) and saturated aqueous NaCl (30 mL). The organic portion is dried over $Na_2SO_4$, filtered, and concentrated under reduced pressure to give 3-[2-methoxy-6-(2-methoxy-4-trifluoromethoxy-phenyl)-5-methyl-pyridin-3-yl]-3H-imidazole-4-carboxylic acid TLC $R_f$ 0.20 (elution with 10% methanol-methylene chloride).

Step 4. Preparation of {3-[2-Methoxy-6-(2-methoxy-4-trifluoromethoxy-phenyl)-5-methyl-pyridin-3-yl]-3H-imidazole-4-yl}-morpholin-4-yl-methanone

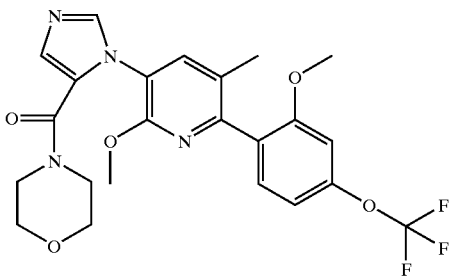

A solution of 3-[2-methoxy-6-(2-methoxy-4-trifluoromethoxy-phenyl)-5-methyl-pyridin-3-yl]-3H-imidazole-4-carboxylic acid (0.2 g, 0.50 mmol), morpholine (0.04 mL, 0.47 mmol) and N,N diisopropylethyl amine (0.1 mL, 0.5 mmol) in $CH_2Cl_2$ (5 mL) is treated with benzotriazol-1-yloxytris-(dimethylamino)phosphonium hexafluorophosphate (0.20 g, 0.50 mmol) and stirred at room temperature overnight. The resulting mixture is diluted with $CH_2Cl_2$ (50 mL) and water (50 mL) and saturated aqueous NaCl (50 mL). The organic portion is dried over $Na_2SO_4$, filtered and concentrated. Purification by preparative TLC (8% methanol-$CH_2Cl_2$) gives {3-[2-methoxy-6-(2-methoxy-4-trifluoromethoxy-phenyl)-5-methyl-pyridin-3-yl]-3H-imidazole-4-yl}-morpholin-4-yl-methanone (Compound 6) as a white solid. TLC $R_f$ 0.45 (elution with 8% methanol-methylene chloride).

Example 7

Preparation of 4-Fluoro-1-methoxy-2-[4-methoxy-2-(6-methoxy -2,4-dimethylphenyl)-6-methylpyrimidin-5-yl]benzene Step 1. Preparation of 4-Methoxy-2-(6-methoxy-2,4-dimethylphenyl)-6-methylpyrimidin-5-ol.

A mixture of 2-chloro-4-methoxy-6-methylpyrimidin-5-ol (348 mg, 2.0 mmol), 2-methoxy-4,6-dimethylphenylboronic acid (540 mg, 3.0 mmol), tetrakis(triphenylphosphine)palladium (0) (115 mg, 5 mol %) in toluene (12 mL) and sodium carbonate (1M in water, 4 mL) is heated at 95° C. (oil bath temperature) in a pressure tube for 14 hours. The reaction is cooled to room temperature, diluted with ethyl acetate, washed with NaOH (2M) and then brine (2×50 mL). The solvents are dried (sodium sulfate) and removed under reduced pressure. Flash chromatography of the crude product (50% ethyl acetate in hexanes) yields 4-methoxy-2-(6-methoxy-2,4-dimethylphenyl)-6-methylpyrimidin-5-ol as a white solid.

Step 2. Preparation of 4-Methoxy-2-(6-methoxy-2,4-dimethylphenyl)-6-methylpyrimidin-5-ylmethylsulfonate.

Triflic anhydride (222 mg, 1.5 mmol) is added to a mixture of 4-methoxy-2-(6-methoxy-2,4-dimethylphenyl)-6-methylpyrimidin-5-ol (274 mg, 1.0 mmol) and triethylamine (202 mg, 2.0 mmol) in dichloromethane. After 0.5 hours the mixture is partitioned between brine and dichloromethane and further extracted with dichloromethane. The organic phase is dried (magnesium sulfate) and the solvents removed under reduced pressure to yield 4-methoxy-2-(6-methoxy-2,4-dimethylphenyl)-6-methylpyrimidin-5-ylmethylsulfonate as an oil.

Step 3. Preparation of 4-Fluoro-1-methoxy-2-[4-methoxy-2-(6-methoxy-2,4-dimethylphenyl)-6-methylpyrimidin-5-yl]benzene.

A mixture of 4-methoxy-2-(6-methoxy-2,4-dimethylphenyl)-6-methylpyrimidin-5-ylmethylsulfonate (203 mg, 0.5 mmol), 2-methoxy-4-fluorophenylboronic acid (169 mg, 1.0 mmol), tetrakis(triphenylphosphine)palladium (0) (29 mg, 5 mol %) in toluene (5 mL) and sodium carbonate (1M in water, 2 mL) is heated at 95° C. (oil bath temperature) in a pressure tube for 14 hours. The reaction is cooled to room temperature, diluted with ethyl acetate, washed with NaOH (2M) and then brine (2×50 mL). The solvents are dried (sodium sulfate) and removed under reduced pressure. Flash chromatography of the crude product (50% ethyl acetate in hexanes) yields 4-fluoro-1-methoxy-2-[4-methoxy-2-(6-methoxy-2,4-dimethylphenyl)-6-methylpyrimidin-5-yl]benzene (Compound 7) as an oil. MS: 383. NMR (400 MHz, $CDCl_3$): 2.14 (s, 3H), 2.28 (s, 3H), 2.35 (s, 3H), 3.76 (s, 3H), 3.77 (s, 3H), 3.88 (s, 3H), 6.66 (s, 1H), 6.70 (s, 1H), 6.91–6.98 (m, 2H), 7.04–7.09 (m, 1H).

Example 8

Additional Compounds of Formula I

Cpd#s 8–38 in the Tables I, II and III may be prepared by the methods shown in Scheme 1 and further illustrated in Examples 1 and 2.

TABLE 1

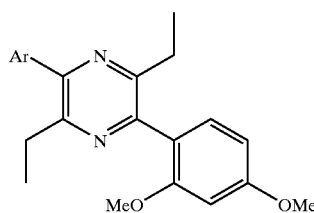

| Cpd# | Ar | $^1$H NMR (CDCl$_3$) | MS (CI) | Name |
|---|---|---|---|---|
| 8 | Phenyl | 1.19(t, 1H), 1.26(t, 1H), 2.67(q, 2H), 2.95(q, 2H), 3.78(s, 3H), 3.87(s, 3H), 6.56(d, 1H), 6.63(dd, 1H), 7.30(d, 1H), 7.4–7.5(m, 3H), 7.63(d, 2H) | 349 | 2-(2,4-Dimethoxy-phenyl)-3,6-diethyl-5-phenyl-pyrazine |
| 9 | o-Tolyl | 1.14(t, 6H), 2.20(s, 3H), 2.68(m, 4H), 3.79(s, 3H), 3.88(s, 3H), 6.57(d, 1H), 6.63(dd, 1H), 7.28(m, 2H), 7.32(m, 3H) | 363 | 2-(2,4-Dimethoxy-phenyl)-3,6-diethyl-(2-methylphenyl)-pyrazine |
| 10 | 2-Trifluoromethylphenyl | 1.12(t, 3H), 1.15(t, 3H), 2.60(m, 2H), 2.67(q, 2H), 3.78(s, 3H), 3.87(s, 3H), 6.57(d, 1H), 6.64(dd, 1H), 7.32(d, 1H), 7.43(d, 1H), 7.55(t, 1H), 7.63(t, 1H), 7.81(d, 1H) | 417 | 2-(2,4-Dimethoxy-phenyl)-3,6-diethyl-5-(2-trifluoromethyl-phenyl)-pyrazine |
| 11 | m-Tolyl | 1.17(t, 3H), 1.23(t, 3H), 2.26(s, 3H), 2.72(q, 2H), 3.76(t, 3H), 3.84(t, 3H), 6.54(m, 1H), 6.60(dd, 1H), 6.68(d, 1H), 7.05(m, 1H), 7.28(d, 1H), 7.34(t, 1H), 7.40(m, 1H) | 363 | 2-(2,4-Dimethoxy-phenyl)-3,6-diethyl-5-(3-methylphenyl)-pyrazine |
| 12 | 3-Trifluoromethylphenyl | 1.19(t, 3H), 1.25(t, 3H), 2.75(q, 2H), 2.95(q, 2H), 3.76(s, 3H), 3.83(s, 3H), 6.52(d, 1H), 6.58(dd, 2H), 7.26(d, 1H), 7.60(t, 1H), 7.68(d, 1H), 7.80(d, 1H), 7.90(s, 1H) | 417 | 2-(2,4-Dimethoxy-phenyl)-3,6-diethyl-5-(3-trifluoromethyl-phenyl)-pyrazine |
| 13 | 2,3-Dimethylphenyl | 1.13(t, 3H), 1.14(t, 3H), 2.06(s, 3H), 2.34(s, 3H), 2.65(m, 4H), 3.78(s, 3H), 3.86(s, 3H), 6.56(d, 1H), 6.62(dd, 1H), 7.1–7.2(m, 3H), 7.31(d, 1H) | 377 | 2-(2,4-Dimethoxy-phenyl)-5-(2,3-dimethyl-phenyl)-3,6-diethyl-pyrazine |
| 14 | 3,5-Dimethylphenyl | 1.19(t, 3H), 1.25(t, 3H), 2.23(s, 3H), 2.39(s, 3H), 2.78(q, 2H), 2.96(q, 2H), 3.78(s, 3H), 3.87(s, 3H), 6.56(d, 1H), 6.63(dd, 1H), 7.07(s, 1H), 7.22(s, 2H), 7.30(d, 1H) | 377 | 2-(2,4-Dimethoxy-phenyl)-5-(3,5-dimethyl-phenyl)-3,6-diethyl-pyrazine |
| 15 | 2,6-Dimethylphenyl | 1.128(t, 3H), 1.130(t, 3H), 2.04(s, 6H), 2.58(q, 2H), 2.72(q, 2H), 3.78(s, 3H), 3.87(s, 3H), 6.57(d, 1H), 6.64(dd, 1H), 7.13(d, 2H), 7.21(m, 1H), 7.33(d, 1H) | 377 | 2-(2,4-Dimethoxy-phenyl)-5-(2,6-dimethyl-phenyl)-3,6-diethyl-pyrazine |
| 16 | 2,4,6-Trimethylphenyl | 1.12(t, 3H), 1.14(t, 3H), 2.01(s, 6H), 2.34(s, 3H), 2.46(q, 2H), 2.68(q, 2H), 3.78(s, 3H), 3.87(s, 3H), 6.57(d, 1H), 6.64(dd, 1H), 6.96(s, 2H), 7.33(d, 1H) | 391 | 2-(2,4-Dimethoxy-phenyl)-(3,6-diethyl-(2,4,6-trimethyl-phenyl)-pyrazine |
| 17 | 2,4-Dimethoxyphenyl | 1.15(t, 6H), 2.64(q, 4H), 3.78(s, 6H), 3.87(s, 6H), 6.56(d, 2H), 6.67(dd, 2H), 7.30(d, 2H) | 417 | 2,5-Bis-(2,4-dimethoxy-phenyl)-(3,6-diethyl-pyrazine |
| 18 | 2-Methoxy-5-fluorophenyl | 1.16(t, 3H), 1.17(t, 3H), 2.64(m, 4H), 3.77(s, 3H), 3.78(s, 3H), 3.86(s, 3H), 6.56(d, 1H), 6.15(dd, 1H), 6.90(dd, 1H), 7.1(m, 2H), 7.30(d, 1H) | 397 | 2-(2,4-Dimethoxy-phenyl)-3,6-diethyl-5-(5-fluoro-2-methoxy-phenyl)-pyrazine |
| 19 | 2-Methoxy-5-chlorophenyl | 1.16(s, 3H), 1.17(t, 3H), 2.65(m, 4H), 3.770(s, 3H), 3.773(s, 3H), 3.86(s, 3H), 6.56(d, 1H), 6.62(dd, 1H), 6.9(d, 1H), 7.29(d, 1H), 7.32–7.36(m, 2H) | 413 | 2-(5-Chloro-2-methoxy-phenyl)-5-(2,4-dimethoxy-phenyl)-3,6-diethyl-pyrazine |
| 20 | 2,5-Dimethoxyphenyl | 1.16(t, 3H), 1.17(s, 3H), 2.68(m, 4H), 3.74(s, 3H), 3.78(s, 3H), 3.80(s, 3H), 3.86(s, 3H), 6.56(d, 1H), 6.62(dd, 1H), 6.94(m, 3H), 7.30(d, 1H) | 409 | 2-(2,4-Dimethoxy-phenyl)-5-(2,5-dimethoxy-phenyl)-3,6-diethyl-pyrazine |
| 21 | 2-Methoxy-5-isopropylphenyl | 1.16(t, 3H), 1.17(t, 3H), 1.23(d, 2H), 1.25(d, 2H), 2.70(q, 2H), 2.90(m, 3H), 3.76(s, 3H), 3.77(s, 3H), 3.85(s, 3H), 6.56(d, 1H), 6.62(dd, 1H), 6.9(d, 1H), 7.2–7.3(m, 3H) | 421 | 2-(2,4-Dimethoxy-phenyl)-3,6-diethyl-5-(5-isopropyl-2-methoxy-phenyl)-pyrazine |
| 22 | 2,5-Dichlorophenyl | 1.15(s, 3H), 1.18(s, 3H), 2.70(m, 4H), 3.78(s, 3H), 3.87(s, 3H), 6.56(d, 1H), 6.63(dd, 1H), 7.30(d, 1H), 7.36(m, 1H), 7.42(m, 1H) | 417 | 2-(2,5-Dichloro-phenyl)-5-(2,4-dimethoxy-phenyl)-3,6-diethyl-pyrazine |
| 23 | 2,3,5-Trichlorophenyl | 1.14(t, 3H), 1.19(t, 1H), 2.72(m, 4H), 3.79(s, 3H), 3.87(s, 3H), 6.54(d, 1H), 6.63(dd, 1H), 7.30(d, 1H), 7.34(d, 1H), 7.56(d, 1H) | 451 | 2-(2,4-Dimethoxy-phenyl)-3,6-diethyl-5-(2,3,5-trichloro-phenyl)-pyrazine |

TABLE 1-continued

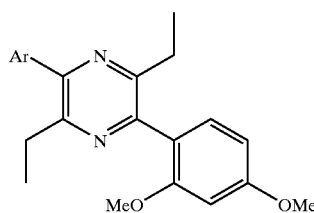

| Cpd# | Ar | $^1$H NMR (CDCl$_3$) | MS (CI) | Name |
|---|---|---|---|---|
| 24 | 3-Methyl-4-fluorophenyl | 1.17(t, 3H), 1.23(t, 3H), 2.34(d, 3H), 2.72(q, 2H), 2.94(q, 2H), 3.76(s, 3H), 3.85(s, 3H), 6.53(d, 1H), 6.60(dd, 1H), 7.08(t, 1H), 7.27(d, 1H), 7.38(m, 1H), 7.43(dd, 1H) | 381 | 2-(2,4-Dimethoxy-phenyl)-3,6-diethyl-5-(4-fluoro-3-methyl-phenyl)-pyrazine |
| 25 | 3-Trifluoromethoxy-phenyl | 1.10(t, 3H), 1.17(t, 3H), 2.64(q, 2H), 2.80(q, 2H), 3.69(s, 3H), 3.76(s, 3H), 6.55(d, 1H), 6.60(dd, 1H), 7.00(t, 1H), 7.2(m, 2H), 7.42(m, 2H) | 433 | 2-(2,4-Dimethoxy-phenyl)-3,6-diethyl-5-(3-trifluoromethoxy-phenyl)-pyrazine |
| 26 | 3,5-bis(trifluoro-methyl)phenyl | 1.21(t, 3H), 1.30(t, 3H), 2.68(q, 2H), 2.90(q, 2H), 3.79(s, 3H), 3.87(s, 3H), 6.56(d, 1H), 6.63(dd, 1H), 7.29(d, 1H), 7.96(s, 1H), 8.12(s, 2H) | 485 | 2-(3,5-Bis-trifluoromethyl-phenyl)-5-(2,4-dimethoxy-phenyl)-3,6-diethyl-pyrazine |
| 27 | 1-Naphthyl | 1.09(t, 3H), 1.17(t, 3H), 2.60(q, 2H), 2.76(q, 2H), 3.82(s, 3H), 3.88(s, 3H), 6.67(d, 1H), 6.63(dd, 1H), 7.37(d, 1H), 7.4–7.4(m, 5H), 7.94(t, 2H) | 399 | 2-(2,4-Dimethoxy-phenyl)-3,6-diethyl-5-naphthalen-1-yl-pyrazine |
| 28 | 2-Naphthyl | 1.21(t, 3H), 1.25(t, 3H), 2.77(q, 2H), 2.95(q, 2H), 3.78(s, 3H), 3.87(s, 3H), 6.58(d, 1H), 6.63(dd, 1H), 7.31(d, 1H), 7.52(m, 2H), 7.74(dd, 1H), 7.90(m, 2H), 7.95(d, 1H), 8.40(s, 1H) | 399 | 2-(2,4-Dimethoxy-phenyl)-3,6-diethyl-5-naphthalen-2-yl-pyrazine |

TABLE II

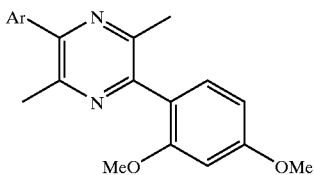

| Cmp# | Ar | $^1$H NMR (CDCl$_3$) | MS (CI) | Name |
|---|---|---|---|---|
| 29 | 2-Methoxy-4-trifluoromethoxy | 2.39(s, 3H), 2.44(s, 3H), 3.81(s, 3H), 3.83(s, 3H), 3.78(s, 3H), 6.56(dd, 1H), 6.63(dd, 1H), 6.84(b, 1H), 6.97(m, 1H), 7.30(d,1H), 7.39(d, 1H) | 435 | 2-(2,4-Dimethoxy-phenyl)-3,6-dimethyl-5-(2-methoxy-4-trifluoromethoxy-phenyl)-pyrazine |
| 30 | o-Tolyl | 2.20(s, 3H), 2.38(s, 3H), 2.43(s, 3H), 3.82(s, 3H), 3.88(s, 3H), 6.58(dd, 1H), 6.62(m, 1H), 7.28(m, 2H), 7.34(m, 3H) | 335 | 2-(2,4-Dimethoxy-phenyl)-3,6-dimethyl-5-(2-methylphenyl)-pyrazine |

TABLE III

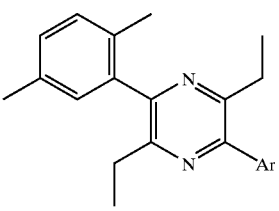

| EX# | Ar | $^1$H NMR (CDCl$_3$) | MS (CI) | Name |
|---|---|---|---|---|
| 31 | 4-(1-Fluoro-1-methyl-ethyl)-2,6-dimethoxy-phenyl | 1.12(t, 6H), 1.70(s, 3H), 1.78(s, 3H), 2.14(s, 3H), 2.38(s, 3H), 2.64(m, 4H), 3.76(s, 6H), 6.68(s, 2H), 7.12(dd, 1H), 7.14(s, 1H), 7.18(dd, 1H) | 437 | 2-(2,5-Dimethyl-phenyl)-3,6-diethyl-5-[4-(1-fluoro-1-methyl-ethyl)-2,6-dimethoxy-phenyl]-pyrazine |
| 32 | 4-(1-Hydroxy-1-methyl- | 1.12(t, 6H), 1.62(s, 6H), 2.14(s, 3H), 2.36 | 435 | 2-{4-[5-(2,5-Dimethyl-phenyl)-3,6- |

TABLE III-continued

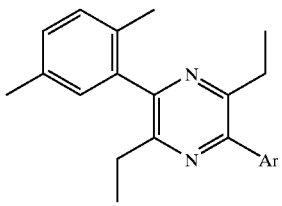

| EX# | Ar | ¹H NMR (CDCl₃) | MS (CI) | Name |
|---|---|---|---|---|
|  | ethyl)-2,6-dimethoxy-phenyl | (s, 3H), 2.62(m, 4H), 3.75(s, 6H), 6.79(s, 2H), 7.12(dd, 1H), 7.14(s, 1H), 7.18(dd, 1H) |  | diethyl-pyrazine-2-yl]-3,5-dimethoxy-phenyl}-propan-2-ol |
| 33 | 4-Acetyl-2,6-dimethoxy-phenyl | 1.10(dt, 6H), 2.14(s, 3H), 2.38(s, 3H), 2.56(q, 2H), 2.66(s, 3H), 2.67(q, 2H), 3.81(s, 6H), 7.12(dd, 1H), 7.14(s, 1H), 7.18(dd, 1H), 7.24(s, 2H) | 419 | 1-{4-[5-(2,5-Dimethyl-phenyl)-3,6-diethyl-pyrazin-2-yl]-3,5-dimethoxy-phenyl}-ethanone |
| 34 | 4-(1-Fluoro-ethyl)-2,6-dimethoxy-phenyl | 1.12(dt, 6H), 1.68(dd, 3H), 2.14(s, 3H), 2.37(s, 3H), 2.58(q, 2H), 2.68(q, 2H), 3.76(s, 3H), 3.78(s, 3H), 5.60-5.80(dq, 1H), 6.60(s, 1H), 6.70(s, 1H), 7.16(dd, 1H), 7.18(s, 1H), 7.20(dd, 1H) | 423 | 2-(2,5-Dimethyl-phenyl)-3,6-diethyl-5-[4-(1-fluoro-ethyl)-2,6-dimethoxy-phenyl]-pyrazine |
| 35 | 4-(1-Hydroxy-ethyl)-2,6-dimethoxy-phenyl | 1.10(t, 6H), 1.59(d, 3H), 2.14(s, 3H), 2.37(s, 3H), 2.58(q, 2H), 2.62(q, 2H), 3.76(s, 3H), 3.78(s, 3H), 4.96(q, 1H), 6.61(s, 1H), 6.72(s, 1H), 7.16(dd, 1H), 7.18(s, 1H), 7.21(dd, 1H) | 421 | 1-{4-[5-(2,5-Dimethyl-phenyl)-3,6-diethyl-pyrazin-2-yl]-3,5-dimethoxy-phenyl}-ethanol |
| 36 | 4-Difluoromethyl-2,6-dimethoxy-phenyl | 1.14(t, 6H), 2.14(s, 3H), 2.48(s, 3H), 2.58(q, 2H), 2.66(q, 2H), 3.82(s, 6H), 6.70(t, 1H), 6.80(s, 2H), 7.16(dd, 1H), 7.18(s, 1H), 7.21(dd, 1H) | 427 | 2-(4-Difluoromethyl-2,6-dimethoxy-phenyl)-5-(2,5-dimethyl-phenyl)-3,6-diethyl-pyrazine |
| 37 | 4-Formyl-2,6-dimethoxy-phenyl | 1.11(dt, 6H), 2.13(s, 3H), 2.37(s, 3H), 2.56(q, 2H), 2.68(q, 2H), 3.84(s, 6H), 7.15(m, 2H), 7.21(m, 3H), 10.01(s, 1H) | 405 | 4-[5-(2,5-Dimethyl-phenyl)-3,6-diethyl-pyrazin-2-yl]-3,5-dimethoxy-benzaldehyde |
| 38 | 4-[1,3]Dioxolan-2-yl-2,6-dimethoxy-phenyl | 1.10(dt, 6H), 2.13(s, 3H), 2.36(s, 3H), 2.58(q, 2H), 2.67(q, 2H), 3.76(s, 6H), 4.10–4.40(m, 4H), 5.68(s, 1H), 6.68(s, 2H), 7.12(dd, 1H), 7.16(s, 1H), 7.18(dd, 1H) | 449 | 2-(2,5-Dimethyl-phenyl)-5-(4-[1,3]dioxolan-2-yl-2,6-dimethoxy-phenyl)-3,6-diethyl-pyrazine |

Compounds 39–94

The following compounds are prepared using the methods given in Scheme I and further illustrated in the preceding examples.

| Cpd# | Ar₁ | Ar₂ |
|---|---|---|
| 39 | 2,5-Dimethoxyphenyl | 4-Isopropyl-2,6-dimethoxyphenyl |
| 40 | 2,5-Dimethoxyphenyl | 4-(1-Fluoro-1-methyl-ethyl)-2,6-dimethoxy-phenyl |
| 41 | 2,5-Dimethoxyphenyl | 4-(1-Hydroxy-1-methyl-ethyl)-2,6-dimethoxy-phenyl |
| 42 | 2,5-Dimethoxyphenyl | 4-Acetyl-2,6-dimethoxy-phenyl |
| 43 | 2,5-Dimethoxyphenyl | 4-(1-Fluoro-ethyl)-2,6-dimethoxy-phenyl |
| 44 | 2,5-Dimethoxyphenyl | 4-(1-Hydroxy-ethyl)-2,6-dimethoxy-phenyl |
| 45 | 2,5-Dimethoxyphenyl | 4-Difluoromethyl-2,6-dimethoxy-phenyl |
| 46 | 2,5-Dimethoxyphenyl | 4-Formyl-2,6-dimethoxy-phenyl |
| 47 | 2,5-Dimethoxyphenyl | 4-[1,3]Dioxolan-2-yl-2,6-dimethoxy-phenyl |
| 48 | 2-Methoxy-5-chlorophenyl | 4-Isopropyl-2,6-dimethoxyphenyl |
| 49 | 2-Methoxy-5-chlorophenyl | 4-(1-Fluoro-1-methyl-ethyl)-2,6-dimethoxy-phenyl |
| 50 | 2-Methoxy-5-chlorophenyl | 4-(1-Hydroxy-1-methyl-ethyl)-2,6-dimethoxy-phenyl |
| 51 | 2-Methoxy-5-chlorophenyl | 4-Acetyl-2,6-dimethoxy-phenyl |
| 52 | 2-Methoxy-5-chlorophenyl | 4-(1-Fluoro-ethyl)-2,6-dimethoxy-phenyl |

-continued

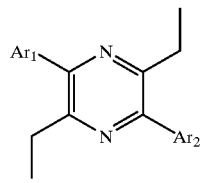

| Cpd# | Ar₁ | Ar₂ |
|---|---|---|
| 53 | 2-Methoxy-5-chlorophenyl | 4-(1-Hydroxy-ethyl)-2,6-dimethoxy-phenyl |
| 54 | 2-Methoxy-5-chlorophenyl | 4-Difluoromethyl-2,6-dimethoxy-phenyl |
| 55 | 2-Methoxy-5-chlorophenyl | 4-Formyl-2,6-dimethoxy-phenyl |
| 56 | 2-Methoxy-5-chlorophenyl | 4-[1,3]Dioxolan-2-yl-2,6-dimethoxy-phenyl |
| 57 | 2-Methoxy-5-chlorophenyl | 4-isopropyl-2,6-dimethoxyphenyl |
| 58 | 2-Methoxy-5-fluorophdnyl | 4-(1-Fluoro-1-methyl-ethyl)-2,6-dimethoxy-phenyl |
| 59 | 2-Methoxy-5-fluorophenyl | 4-(1-Hydroxy-1-methyl-ethyl)-2,6-dimethoxy-phenyl |
| 60 | 2-Methoxy-5-fluorophenyl | 4-Acetyl-2,6-dimethoxy-phenyl |
| 61 | 2-Methoxy-5-fluorophenyl | 4-(1-Fluoro-ethyl)-2,6-dimethoxy-phenyl |
| 62 | 2-Methoxy-5-fluorophenyl | 4-(1-Hydroxy-ethyl)-2,6-dimethoxy-phenyl |
| 63 | 2-Methoxy-5-fluorophenyl | 4-Difluoromethyl-2,6-dimethoxy-phenyl |
| 64 | 2-Methoxy-5-fluorophenyl | 4-Formyl-2,6-dimethoxy-phenyl |
| 65 | 2-Methoxy-5-fluorophenyl | 4-[1,3]Dioxolan-2-yl-2,6-dimethoxy-phenyl |
| 66 | 2-Methoxy-5-fluorophenyl | 4-Isopropyl-2,6-dimethoxyphenyl |
| 67 | 2,5-Dichlorophenyl | 4-(1-Fluoro-1-methyl-ethyl)-2,6-dimethoxy-phenyl |
| 68 | 2,5-Dichlorophenyl | 4-(1-Hydroxy-1-methyl-ethyl)-2,6-dimethoxy-phenyl |
| 69 | 2,5-Dichlorophenyl | 4-Acetyl-2,6-dimethoxy-phenyl |
| 70 | 2,5-Dichlorophenyl | 4-(1-Fluoro-ethyl)-2,6-dimethoxy-phenyl |
| 71 | 2,5-Dichlorophenyl | 4-(1-Hydroxy-ethyl)-2,6-dimethoxy-phenyl |
| 72 | 2,5-Dichlorophenyl | 4-Difluoromethyl-2,6-dimethoxy-phenyl |
| 73 | 2,5-Dichlorophenyl | 4-Formyl-2,6-dimethoxy-phenyl |
| 74 | 2,5-Dichlorophenyl | 4-[1,3]Dioxolan-2-yl-2,6-dimethoxy-phenyl |
| 75 | 2,5-Dichlorophenyl | 4-Isopropyl-2,6-dimethoxyphenyl |
| 76 | 2-Methoxy-5-isopropyl | 4-(1-Fluoro-1-methyl-ethyl)-2,6-dimethoxy-phenyl |
| 77 | 2-Methoxy-5-isopropyl | 4-(1-Hydroxy-1-methyl-ethyl)-2,6-dimethoxy-phenyl |
| 78 | 2-Methoxy-5-isopropyl | 4-Acetyl-2,6-dimethoxy-phenyl |
| 79 | 2-Methoxy-5-isopropyl | 4-(1-Fluoro-ethyl)-2,6-dimethoxy-phenyl |
| 80 | 2-Methoxy-5-isopropyl | 4-(1-Hydroxy-ethyl)-2,6-dimethoxy-phenyl |
| 81 | 2-Methoxy-5-isopropyl | 4-Difluoromethyl-2,6-dimethoxy-phenyl |
| 82 | 2-Methoxy-5-isopropyl | 4-Formyl-2,6-dimethoxy-phenyl |
| 83 | 2-Methoxy-5-isopropyl | 4-[1,3]Dioxolan-2-yl-2,6-dimethoxy-phenyl |
| 84 | 2-Methoxy-5-isopropyl | 4-Isopropyl-2,6-dimethoxyphenyl |
| 85 | 2-Methoxy-5-isopropyl | 4-(1-Fluoro-1-methyl-ethyl)-2,6-dimethoxy-phenyl |
| 86 | 2,5-Difluorophenyl | 4-(1-Hydroxy-1-methyl-ethyl)-2,6-dimethoxy-phenyl |
| 87 | 2,5-Difluorophenyl | 4-Acetyl-2,6-dimethoxy-phenyl |
| 88 | 2,5-Difluorophenyl | 4-(1-Fluoro-ethyl)-2,6-dimethoxy-phenyl |
| 89 | 2,5-Difluorophenyl | 4-(1-Hydroxy-ethyl)-2,6-dimethoxy-phenyl |
| 90 | 2,5-Difluorophenyl | 4-Difluoromethyl-2,6-dimethoxy-phenyl |
| 91 | 2,5-Difluorophenyl | 4-Formyl-2,6-dimethoxy-phenyl |
| 92 | 2,5-Difluorophenyl | 4-[1,3]Dioxolan-2-yl-2,6-dimethoxy-phenyl |
| 93 | 2,5-Difluorophenyl | 4-Isopropyl-2,6-dimethoxyphenyl |
| 94 | 2,5-Difluorophenyl | 4-(1-Fluoro-1-methyl-ethyl)-2,6-dimethoxy-phenyl |

Compounds 95–153

The following compounds can be prepared using the methods given in reaction scheme II and further illustrated in example 7.

TABLE IV

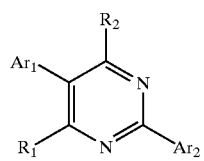

| Cpd# | Ar₁ | R₁ | R₂ | Ar₂ |
|---|---|---|---|---|
| 95 | 2-Methoxy-5-fluorophenyl | C₂H₅ | OCH₃ | 6-Methoxy-2,4-dimethylphenyl |
| 96 | 2-Methoxy-5-fluorophenyl | CH₃ | OCH₃ | 4-Isopropyl-2,6-dimethoxyphenyl |
| 97 | 2-Methoxy-5-fluorophenyl | C₂H₅ | OCH₃ | 4-Isopropyl-2,6-dimethoxyphenyl |

TABLE IV-continued

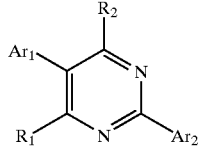

| Cpd# | Ar$_1$ | R$_1$ | R$_2$ | Ar$_2$ |
|---|---|---|---|---|
| 98 | 2-Methoxy-5-fluorophenyl | CH$_3$ | OCH$_3$ | 2,6-Dichloro-4-methoxyphenyl |
| 99 | 2-Methoxy-5-fluorophenyl | C$_2$H$_5$ | OCH$_3$ | 2,6-Dichloro-4-methoxyphenyl |
| 100 | 2-Methoxy-5-fluorophenyl | CH$_3$ | OCH$_3$ | 2,4,6-Trimethylphenyl |
| 101 | 2-Methoxy-5-fluorophenyl | C$_2$H$_5$ | OCH$_3$ | 2,4,6-Trimethylphenyl |
| 102 | 2-Methoxy-5-fluorophenyl | C$_2$H$_5$ | OC$_2$H$_5$ | 6-Methoxy-2,4-dimethylphenyl |
| 103 | 2-Methoxy-5-fluorophenyl | CH$_3$ | OCH$_3$ | 2,6-Dimethoxy-4-chlorophenyl |
| 104 | 2-Methoxy-5-fluorophenyl | C$_2$H$_5$ | OCH$_3$ | 2,6-Dimethoxy-4-chlorophenyl |
| 105 | 2-Methoxy-5-chlorophenyl | C$_2$H$_5$ | OCH$_3$ | 6-Methoxy-2,4-dimethylphenyl |
| 106 | 2-Methoxy-5-chlorophenyl | CH$_3$ | OCH$_3$ | 4-Isopropyl-2,6-dimethoxyphenyl |
| 107 | 2-Methoxy-5-chlorophenyl | C$_2$H$_5$ | OCH$_3$ | 4-Isopropyl-2,6-dimethoxyphenyl |
| 108 | 2-Methoxy-5-chlorophenyl | CH$_3$ | OCH$_3$ | 2,6-Dichloro-4-methoxyphenyl |
| 109 | 2-Methoxy-5-chlorophenyl | C$_2$H$_5$ | OCH$_3$ | 2,6-Dichloro-4-methoxyphenyl |
| 110 | 2-Methoxy-5-chlorophenyl | CH$_3$ | OCH$_3$ | 2,4,6-Trimethylphenyl |
| 111 | 2-Methoxy-5-chlorophenyl | C$_2$H$_5$ | OCH$_3$ | 2,4,6-Trimethylphenyl |
| 112 | 2-Methoxy-5-chlorophenyl | C$_2$H$_5$ | OCH$_3$ | 6-Methoxy-2,4-dimethylphenyl |
| 113 | 2-Methoxy-5-chlorophenyl | CH$_3$ | OCH$_3$ | 2,6-Dimethoxy-4-chlorophenyl |
| 114 | 2-Methoxy-5-chlorophenyl | C$_2$H$_5$ | OCH$_3$ | 2,6-Dimethoxy-4-chlorophenyl |
| 115 | 2,5-Dimethoxyphenyl | C$_2$H$_5$ | OCH$_3$ | 6-Methoxy-2,4-dimethylphenyl |
| 116 | 2,5-Dimethoxyphenyl | CH$_3$ | OCH$_3$ | 4-Isopropyl-2,6-dimethoxyphenyl |
| 117 | 2,5-Dimethoxyphenyl | C$_2$H$_5$ | OCH$_3$ | 4-Isopropyl-2,6-dimethoxyphenyl |
| 118 | 2,5-Dimethoxyphenyl | CH$_3$ | OCH$_3$ | 2,6-Dichloro-4-methoxyphenyl |
| 119 | 2,5-Dimethoxyphenyl | C$_2$H$_5$ | OCH$_3$ | 2,6-Dichloro-4-methoxyphenyl |
| 120 | 2,5-Dimethoxyphenyl | CH$_3$ | OCH$_3$ | 2,4,6-Trimethylphenyl |
| 121 | 2,5-Dimethoxyphenyl | C$_2$H$_5$ | CH$_3$ | 2,4,6-Trimethylphenyl |
| 122 | 2,5-Dimethoxyphenyl | C$_2$H$_5$ | OC$_2$H$_5$ | 6-Methoxy-2,4-dimethylphenyl |
| 123 | 2,5-Dimethoxyphenyl | CH$_3$ | OCH$_3$ | 2,6-Dimethoxy-4-chlorophenyl |
| 124 | 2,5-Dimethoxyphenyl | C$_2$H$_5$ | OCH$_3$ | 2,6-Dimethoxy-4-Chlorophenyl |
| 125 | 2,5-Dichlorophenyl | C$_2$H$_5$ | OCH$_3$ | 6-Methoxy-2,4-dimethylphenyl |
| 126 | 2,5-Dichlorophenyl | CH$_3$ | OCH$_3$ | 4-Isopropyl-2,6-dimethoxyphenyl |
| 127 | 2,5-Dichlorophenyl | C$_2$H$_5$ | OCH$_3$ | 4-Isopropyl-2,6-dimethoxyphenyl |
| 128 | 2,5-Dichlorophenyl | CH$_3$ | OCH$_3$ | 2,6-Dichloro-4-methoxyphenyl |
| 129 | 2,5-Dichlorophenyl | C$_2$H$_5$ | OCH$_3$ | 2,6-Dichloro-4-methoxyphenyl |
| 130 | 2,5-Dichlorophenyl | CH$_3$ | OCH$_3$ | 2,4,6-Trimethylphenyl |
| 131 | 2,5-Dichlorophenyl | C$_2$H$_5$ | OCH$_3$ | 2,4,6-Trimethylphenyl |
| 132 | 2,5-Dichlorophenyl | C$_2$H$_5$ | OC$_2$H$_5$ | 6-Methoxy-2,4-dimethylphenyl |
| 133 | 2,5-Dichlorophenyl | CH$_3$ | CH$_3$ | 2,6-Dimethoxy-4-chlorophenyl |
| 134 | 2,5-Dichlorophenyl | C$_2$H$_5$ | CH$_3$ | 2,6-Dimethoxy-4-chlorophenyl |
| 135 | 2-Methoxy-5-isopropyl | C$_2$H$_5$ | OCH$_3$ | 6-Methoxy-2,4-dimethylphenyl |
| 136 | 2-Methoxy-5-isopropyl | CH$_3$ | OCH$_3$ | 4-Isopropyl-2,6-dimethoxyphenyl |
| 137 | 2-Methoxy-5-isopropyl | C$_2$H$_5$ | CH$_3$ | 4-Isopropyl-2,6-dimethoxyphenyl |
| 138 | 2-Methoxy-5-isopropyl | CH$_3$ | OCH$_3$ | 2,6-Dichloro-4-methoxyphenyl |
| 139 | 2-Methoxy-5-isopropyl | C$_2$H$_5$ | OCH$_3$ | 2,6-Dichloro-4-methoxyphenyl |
| 140 | 2-Methoxy-5-isopropyl | CH$_3$ | OCH$_3$ | 2,4,6-Trimethylphenyl |
| 141 | 2-Methoxy-5-isopropyl | C$_2$H$_5$ | OCH$_3$ | 2,4,6-Trimethylphenyl |
| 142 | 2-Methoxy-5-isopropyl | C$_2$H$_5$ | OC$_2$H$_5$ | 6-Methoxy-2,4-dimethylphenyl |
| 143 | 2-Methoxy-5-isopropyl | CH$_3$ | OCH$_3$ | 2,6-Dimethoxy-4-chlorophenyl |
| 144 | 2-Methoxy-5-isopropyl | C$_2$H$_5$ | CCH$_3$ | 2,6-Dimethoxy-4-chlorophenyl |
| 145 | 2,5-Difluorophenyl | C$_2$H$_5$ | OCH$_3$ | 6-Methoxy-2,4-dimethylphenyl |
| 146 | 2,5-Difluorophenyl | CH$_3$ | CH$_3$ | 4-Isopropyl-2,6-dimethoxyphenyl |
| 147 | 2,5-Difluorophenyl | C$_2$H$_5$ | OCH$_3$ | 4-Isopropyl-2,6-dimethoxyphenyl |
| 148 | 2,5-Difluorophenyl | CH$_3$ | CH$_3$ | 2,6-Dichloro-4-methoxyphenyl |
| 149 | 2,5-Difluorophenyl | C$_2$H$_5$ | CCH$_3$ | 2,6-Dichloro-4-methoxyphenyl |
| 150 | 2,5-Difluorophenyl | CH$_3$ | CH$_3$ | 2,4,6-Trimethylphenyl |
| 151 | 2,5-Difluorophenyl | C$_2$H$_5$ | OCH$_3$ | 2,4,6-Trimethylphenyl |
| 152 | 2,5-Difluorophenyl | C$_2$H$_5$ | OC$_2$H$_5$ | 6-Methoxy-2,4-dimethylphenyl |
| 153 | 2,5-Difluorophenyl | CH$_3$ | OCH$_3$ | 2,6-Dimethoxy-4-chlorophenyl |

Example 154–160

The following compounds can be prepared using the methods shown in reaction scheme IIII.

TABLE V

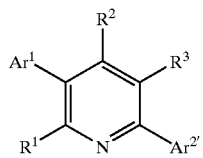

| EX# | Ar¹ | R¹ | R² | R³ | Ar² |
|---|---|---|---|---|---|
| 154 | 2-Methoxy-5-fluorophenyl | $C_2H_5$ | $OCH_3$ | $OCH_3$ | 6-Methoxy-2,4-dimethylphenyl |
| 155 | 2-Methoxy-5-fluorophenyl | $CH_3$ | H | $CH_3$ | 4-Isopropyl-2,6-dimethoxyphenyl |
| 156 | 2-Methoxy-5-fluorophenyl | $C_2H_5$ | $C_2H_5$ | $CH_3$ | 4-Isopropyl-2,6-dimethoxyphenyl |
| 157 | 2-Methoxy-5-fluorophenyl | $CH_3$ | $OCH_3$ | $OCH_3$ | 2,6-Dichloro-4-methoxyphenyl |
| 158 | 2-Methoxy-5-fluorophenyl | $C_2H_5$ | H | $C_2H_5$ | 2,6-Dichloro-4-methoxyphenyl |
| 159 | 2-Methoxy-5-fluorophenyl | $CH_3$ | $CH_3$ | $CH_3$ | 2,4,6-Trimethylphenyl |
| 160 | 2-Methoxy-5-fluorophenyl | $C_2H_5$ | $CH_3$ | $C_2H_5$ | 2,4,6-Trimethylphenyl |
| 161 | 1-(1-Ethyl-propyl)-1H-imidazol-2-yl | $CH_3NH$ | H | $C_2H_5$ | 2-methoxy-4-isopropyl-phenyl |
| 162 | 3,5-dimethyl-pyrazol-1-yl | $CH_3O$ | H | $C_2H_5$ | 2-methoxy-4-isopropyl-phenyl |
| 163 | 3-methyl-5-ethyl-pyrazol-1-yl | $CH_3O$ | H | $C_2H_5$ | 2-methoxy-4-isopropyl-phenyl |

TABLE VI

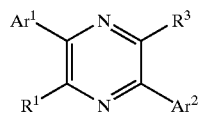

| EX# | Ar¹ | R¹ | R³ | Ar² |
|---|---|---|---|---|
| 164 | 2-Methoxy-5-fluorophenyl | $C_2H_5$ | $OCH_3$ | 6-Methoxy-2,4-dimethylphenyl |
| 165 | 2-Methoxy-5-fluorophenyl | $CH_3$ | $CH_3$ | 4-Isopropyl-2,6-dimethoxyphenyl |
| 166 | 1-(1-Ethyl-propyl)-1H-imidazol-2-yl | $CH_3NH$ | $C_2H_5$ | 2-methoxy-4-isopropyl-phenyl |
| 167 | 3,5-dimethyl-pyrazol-1-yl | $CH_3O$ | $C_2H_5$ | 2-methoxy-4-isopropyl-phenyl |
| 168 | 3-methyl-5-ethyl-pyrazol-1-yl | $CH_3O$ | $C_2H_5$ | 2-methoxy-4-isopropyl-phenyl |

Example 9

Assay for CRF Receptor Binding Activity

As discussed above, the following assay is defined herein as a standard in vitro CRF receptor binding assay. The pharmaceutical utility of compounds of this invention is indicated by the following assay for CRF1 receptor activity.

The CRF receptor binding is performed using a modified version of the assay described by Grigoriadis and De Souza (*Methods in Neurosciences*, Vol. 5, 1991). IMR-32 human neuroblastoma cells, a cell line that can be induced to express the CRF1 receptor, are cultured in growth medium consisting of EMEM w/Earle's BSS (JRH Biosciences, Cat#51411) supplemented with 10% Fetal Bovine Serum, 25 mM HEPES (pH 7.2), 1 mM Sodium Pyruvate, and Non-Essential Amino Acids (JRH Biosciences, Cat#58572). Stock cultures of cells are grown to confluence and subcultured twice per week at split ratios of 1:2 to 1:4 (cells are dislodged during subculturing using No-Zyme, JRH Biosciences, Cat#59226). To induce CRF1 receptor expression, the cells are grown to approximately 80% confluence and then changed to growth media containing 2.5 μM 5-bromo-2'deoxyuridine (BrdU, Sigma, Cat#B9285). Growth media containing BrdU is replaced every 3–4 days and the cells are harvested via centrifugation (using No-Zyme) after 10 days of BrdU treatment. Harvested cells are stored frozen at −80° C. until needed for the preparation of membrane homogenates.

To prepare receptor-containing membranes cells are homogenized in wash buffer (50 mM Tris HCl, 10 mM $MgCl_2$, 2 mM EGTA, pH 7.4) and centrifuged at 48,000×g for 10 minutes at 4° C. The pellet is re-suspended in wash buffer and the homogenization and centrifugation steps are performed once more.

Membrane pellets (containing CRF receptors) are resuspended and brought to a final concentration of 1.0 mg membrane protein/ml in binding buffer (Tris buffer above with 0.1% BSA and 0.1 mM bacitracin.). For the binding assay, 150 microliters of the membrane preparation is added to 96 well microtube plates containing 50 microliters of $^{125}$I-CRF (SA 2200 Ci/mmol, final concentration of 100 pM) and 2 microliters of test compound. Binding is carried out at room temperature for 2 hours. Plates are then harvested using 50 mM Tris buffer pH 7.4, on a BRANDEL 96 well cell harvester and filters (soaked in 1% PEI for 1.5 hours) are counted for gamma emissions on a Wallac 1205 BETA-PLATE liquid scintillation counter. Non-specific binding is defined by 2 micromolar cold CRF. $IC_{50}$ values are calculated with the non-linear curve fitting program RS/1 (BBN Software Products Corp., Cambridge, Mass.).

The binding affinity for the compounds of Formula I expressed as $IC_{50}$ value, generally ranges from about 0.5 nanomolar to about 10 micromolar. Preferred compounds of Formula I exhibit $IC_{50}$ values of less than or equal to 1.5 micromolar, more preferred compounds of Formula I exhibit $IC_{50}$ values of less than 500 nanomolar, still more preferred compounds of Formula I exhibit $IC_{50}$ values of less than 100 nanomolar, and most preferred compound of Formula I exhibit $IC_{50}$ values of less than 10 nanomolar.

The compounds shown in Examples 1–7 have been tested in this assay and found to exhibit $IC_{50}$ values of less than or equal to 4 micromolar.

Example 10

Preparation of Radiolabeled Probe Compounds of Formula I

The compounds of Formula I are prepared as radiolabeled probes by carrying out their synthesis using precursors comprising at least one atom that is a radioisotope. The radioisotope is preferably selected from of at least one of carbon (preferably $^{14}$C), hydrogen (preferably $^{3}$H), sulfur (preferably $^{35}$S), or iodine (preferably $^{125}$I). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of Formula I as substrate. In addition, certain precursors may be subjected to tritium-halogen exchange with tritium gas, tritium gas reduction of unsaturated bonds, or reduction using sodium borotritide, as appropriate.

Example 11

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of Formula I prepared as described in the preceding Examples.

Example 12

Additional Aspects of Preferred Compounds of the Invention

The most preferred compounds of Formula I are suitable for pharmaceutical use in treating human patients. Accordingly, such preferred compounds are non-toxic. They do not exhibit single or multiple dose acute or long-term toxicity, mutagenicity (e.g., as determined in a bacterial reverse mutation assay such as an Ames test), teratogenicity, tumorogenicity, or the like, and rarely trigger adverse effects (side effects) when administered at therapeutically effective dosages.

Preferably, administration of such preferred compounds of Formula I at certain doses (e.g., doses yielding therapeutically effective in vivo concentrations or preferably doses of 10, 50, 100, 150, or 200 mg/kg—preferably 150 mg/kg—administered parenterally or preferably orally) does not result in prolongation of heart QT intervals (i.e., as determined by electrocardiography, e.g., in guinea pigs, minipigs or dogs). When administered daily for 5 or preferably ten days, such doses of such preferred compounds also do not cause liver enlargement resulting in an increase of liver to body weight ratio of more than 100%, preferably not more than 75% and more preferably not more than 50% over matched controls in laboratory rodents (e.g., mice or rats). In another aspect such doses of such preferred compounds also preferably do not cause liver enlargement resulting in an increase of liver to body weight ratio of more than 50%, preferably preferably not more than 25%, and more preferably not more than 10% over matched untreated controls in dogs or other non-rodent animals.

In yet another aspect such doses of such preferred compounds also preferably do not promote the release of liver enzymes (e.g., ALT, LDH, or AST) from hepatocytes in vivo. Preferably such doses do not elevate such enzymes by more than 100%, preferably not by more than 75% and more preferably not by more than 50% over matched untreated controls in laboratory rodents. Similarly, concentrations (in culture media or other such solutions that are contacted and incubated with cells in vitro) equivalent to two, fold, preferably five-fold, and most preferably ten-fold the minimum in vivo therapeutic concentration do not cause release of any of such liver enzymes from hepatocytes in vitro.

Because side effects are often due to undesirable receptor activation or antagonism, preferred compounds of Formula I exert their receptor-modulatory effects and bind to the CRF1 receptor with high selectivity. This means that they do not bind to certain other receptors (i.e., other than CRF receptors) with high affinity, but rather only bind to, activate, or inhibit the activity of such other receptors with affinity constants of greater than 100 nanomolar, preferably greater than 1 micromolar, more preferably greater than 10 micromolar and most preferably greater than 100 micromolar. Such receptors preferably are selected from the group including ion channel receptors, including sodium ion channel receptors, neurotransmitter receptors such as alpha- and beta-adrenergic receptors, muscarinic receptors (particularly m1, m2, and m3 receptors), dopamine receptors, and metabotropic glutamate receptors; and also include histamine receptors and cytokine receptors, e.g., interleukin receptors, particularly IL-8 receptors. The group of other receptors to which preferred compounds do not bind with high affinity also includes $GABA_A$ receptors, bioactive peptide receptors (including NPY and VIP receptors), neurokinin receptors, bradykinin receptors (e.g., BK1 receptors and BK2 receptors), and hormone receptors (including thyrotropin releasing hormone receptors and melanocyte-concentrating hormone receptors).

Example 13

Absence of Sodium Ion Channel Activity

Preferred compounds of Formula I do not exhibit activity as Sodium ion channel blockers. Sodium channel activity may be measured a standard in vitro sodium channel binding assays such as the assay given by Brown et al. (J. Neurosci. (1986) 265: 17995–18004). Preferred compounds of Formula I exhibit less than 15 percent inhibition, and more preferably less than 10 percent inhibition, of sodium channel specific ligand binding when present at a concentration of 4 uM. The sodium ion channel specific ligand used may be labeled batrachotoxinin, tetrodotoxin, or saxitoxin. Such assays, including the assay of Brown referred to above, are performed as a commercial service by CEREP, INC., Redmond, Wash.

Alternatively, sodium ion channel activity may be measured in vivo in an assay of anti-epileptic activity. Anti-epileptic activity of compounds may be measured by the ability of the compounds to inhibit hind limb extension in the supra maximal electro shock model. Male Han Wistar rats (150–200 mg) are dosed i.p. with a suspension of 1 to 20 mg of test compound in 0.25% methylcellulose 2 hr. prior to test. A visual observation is carried out just prior to testing for the presence of ataxia. Using auricular electrodes a current of 200 mA, duration 200 millisec, is applied and the presence or absence of hind limb extension is noted. Preferred compounds of Formula I do not exhibit significant anti-epileptic activity at the $p<0.1$ level of significance or more preferably at the $p<0.05$ level of significance as measured using a standard parametric assay of statistical significance such as a student's T test.

Example 14

Optimal in Vitro Half-Life

Compound half-life values ($t_{1/2}$ values) may be determined via the following standard liver microsomal half-life assay. Liver microsomes are obtained from pooled liver samples and prepared so that the P-450 enzyme content is approximately 0.5 mmol/ mg protein. Reactions are preformed in a 5 ml well deep-well plate as follows:
Phosphate buffer: 19 mL 0.1 M $NaH_2PO_4$, 81 mL 0.1 $Na_2HPO_4$, pH 7.4 with $H_3PO_4$.
CoFactor Mixture: 16.2 mg NADP, 45.4 mg Glucose-6-phosphate in 4 ML 100 mM $MgCl_2$. Glucose-6-phosphate dehydrogenase: 214.3 microliters glucose-6-phosphate dehydrogenase, 1285.7 microlitersdistilled water
Starting Reaction Mixture: 3 mL CoFactor Mixture, 1.2 mL Glucose-6-phosphate dehydrogenase
6 identical sample wells each containing 25 microliters microsomes, 5 microliters test compound (from a 100 uM stock), and 399 microliters 0.1 M phosphate buffer, pH 7.4, are prepared. A seventh well containing 25 microliters microsomes, 399 microliters 0.1 M phosphate buffer, pH 7.4, and 5 microliters(from a 100 uM stock) of a compound, e.g. DIAZEPAM, CLOZEPINE, with known metabolic properties is used as a positive control. Reactions are pre-incubated at 39° C. for 10 minutes. 71 microliters Starting Reaction Mixture is added to 5 of the 6 reaction wells and to the positive control well, 71 microliters 100 mM $MgCl_2$ is added to the sixth reaction well, which is used as a negative control. At each time point (0, 1, 3, 5, and 10 minutes) 75 microliters reaction is pipetted into a 96-well deep-well plate reaction well containing 75 microliters ice-cold acetonitrile. Samples are vortexed and centrifuged 10 minutes at 6000 rpm (Sorval T 6000D rotor). Supernatant, 75 microliters from each reaction well, is transferred to a 96-well plate containing 150 microliters internal standard per well. The remaining test compound is quantitated via LCMS. Compound concentration vs time is plotted and commercially available statistical software is used to extrapolate to the $t_{1/2}$ value of the test compound.

Preferred compounds of Formula I exhibit in vitro $t_{1/2}$ values of greater than 10 minutes and less than 4 hours. Most preferred compounds of Formula I exhibit in vitro $t_{1/2}$ values of between 30 minutes and 1 hour in human liver microsomes.

Example 15

MDCK Toxicity

Compounds causing acute cytotoxicity will decrease ATP production by Madin Darby canine kidney (MDCK) cells in the following assay.

MDCK cells, ATCC no. CCL-34 (American Type Culture Collection, Manassas, Va.) are maintained in sterile conditions following the instructions in the ATCC production information sheet. The PACKARD, (Meriden, Conn.) ATP-LITE-M Luminescent ATP detection kit, product no. 6016941, allows measurement ATP production in MDCK cells.

Prior to assay 1 microliter of test compound or control sample is pipetted into PACKARD (Meriden, Conn.) clear bottom 96-well plates. Test compounds and control samples are diluted in DMSO to give final concentration in the assay of 10 micromolar, 100 micromolar, or 200 micromolar. Control samples are drug or other compounds having known toxicity properties.

Confluent MDCK cells are trypsinized, harvested, and diluted to a concentration of $0.1 \times 10^6$ cells/ ml with warm (37° C.) VITACELL Minimum Essential Medium Eagle (ATCC catalog #30–2003). 100 microliters of cells in medium is pipetted into each of all but five wells of each 96-well plate. Warm medium without cells (100 ul) is pipetted in the remaining five wells of each plate. These wells, to which no cells are added, are used to determine the standard curve. The plates are then incubated at 37° C. under 95% $O_2$, 5% $CO_2$ for 2 hours with constant shaking. After incubation, 50 microliters of mammalian cell lysis solution is added per well, the wells are covered with PACKARD TOPSEAL stickers, and plates are shaken at approximately 700 rpm on a suitable shaker for 2 minutes.

During the incubation, PACKARD ATP LITE-M reagents are allowed to equilibrate to room temperature. Once equilibrated the lyophilized substrate solution is reconstituted in 5.5 m of substrate buffer solution (from kit). Lyophilized ATP standard solution is reconstituted in deionized water to give a 10 mM stock. For the five control wells, 10 microliters of serially diluted PACKARD standard is added to each of the five standard curve control wells to yield a final concentration in each subsequent well of 200 nM, 100 nM, 50 nM, 25 nM, and 12.5 nM.

PACKARD substrate solution (50 ul) is added to all wells. Wells are covered with PACKARD TOPSEAL stickers, and plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter, e.g. PACKARD TOPCOUNT Microplate Scintillation and Luminescense Counter or TECAN SPECTRAFLUOR PLUS.

Luminescence values at each drug concentration are compared to the values computed from the standard curve for that concentration. Preferred test compounds exhibit luminescence values 80% or more of the standard, or preferably 90% or more of the standard, when a 10 micromolar (uM) concentration of the test compound is used. When a 100

What is claimed is:

1. A compound of Formula I

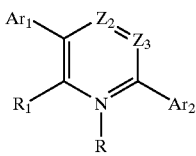

Formula I or a pharmaceutically acceptable salt thereof, wherein:

R is oxygen or absent;

$Z_2$ is $CR_2$;

$Z_3$ is nitrogen;

$Ar_1$ is selected from the group consisting of:

phenyl which is mono-, di-, or tri-substituted with $R_A$, and 1-naphthyl, 2-naphthyl, pyridyl, pyrimidinyl, pyrazinyl, pyrimidinyl, thienyl, thiazolyl, pyrazolyl, imidazolyl, tetrazolyl, oxazolyl, isoxazolyl, pyrrolyl, furanyl, and triazolyl, each of which is optionally mono-, di-, or tri-substituted with $R_A$;

$Ar_2$ is phenyl or pyridyl, each of which is substituted with at a $R_A$ group ortho to the point of attachment of $Ar_2$ in Formula I and is further substituted with one or two additional $R_A$ groups;

$R_1$ and $R_2$ are independently selected from hydrogen, halogen, hydroxy, cyano, amino, nitro, $C_1$–$C_6$alkyl$_1$, $C_1$–$C_6$alkyl$_1$—O—, mono- or di-($C_1$–$C_6$alkyl$_1$)amino, $C_3$–$C_7$cycloalkyl$_2$($C_0$–$C_4$alkyl$_1$), $C_3$–$C_7$cycloalkenyl$_2$ ($C_0$–$C_4$alkyll$_1$), $C_3$–$C_7$cycloalkyl$_2$($C_0$–$C_4$alkyl$_1$)—O—, $C_3$–$C_7$ cycloalkenyl$_2$($C_0$–$C_4$alkyl$_1$)—O—, halo$C_1$–$C_6$alkyl$_1$, halo$C_1$–$C_6$akyl$_1$—O—, and —S(O)$_n$($C_1$–$C_6$alkyl$_1$), where each alkyl$_1$ is independently straight or branched, contains 0 or 1 or more double or triple bonds, and is unsubstituted or substituted with one or more substituents independently chosen from halogen, hydroxy, oxo, cyano, $C_1$–$C_4$alkoxy, amino, and mono- or di-($C_1$–$C_4$alkyl)amino, and where each $C_3$–$C_7$cycloalkyl$_2$ and $C_3$–$C_7$cycloalkenyl$_2$ is optionally substituted by one or more substituents independently chosen from halogen, hydroxy, oxo, cyana, $C_1$–$C_4$alkoxy, amino, and mono- or di-($C_1$–$C_4$)alkylamino, with the proviso that at least one of $R_1$ and $R_2$ is not hydrogen;

$R_A$ is independently selected at each occurrence from halogen, cyano, nitro, halo($C_1$–$C_6$)alkyl, halo($C_1$–$C_6$) alkoxy, hydroxy, amino, $C_1$–$C_6$alkyl substituted with 0–2 $R_B$, $C_2$–$C_6$alkenyl substituted with 0–2 $R_B$, $C_2$–$C_6$alkynyl substituted with 0–2 $R_B$, $C_3$–$C_7$cycloalkyl substituted with 0–2 $R_B$, ($C_3$–$C_7$cycloalkyl)$C_1$–$C_4$alkyl substituted with 0–2 $R_B$, $C_1$–$C_6$alkoxy substituted with 0–2 $R_B$, —NH($C_1$–$C_6$alkyl) substituted with 0–2 $R_B$, —N($C_1$–$C_6$alkyl)($C_1$–$C_6$alkyl) where each $C_1$–$C_6$alkyl is independently substituted with 0–2 $R_B$, and —$XR_C$;

$R_B$ is independently selected at each occurrence from halogen, hydroxy, cyano, amino, $C_1$–$C_4$alkyl, $C_1$–$C_4$alkoxy, mono- or di-($C_1$–$C_4$alkyl)amino, —S(O)$_n$(alkyl), halo($C_1$–$C_4$)alkyl, halo($C_1$–$C_4$)alkoxy, —CO($C_1$–$C_4$alkyl), —CONH($C_1$–$C_4$alkyl), —CON ($C_1$–$C_4$alkyl)($C_1$–$C_4$alkyl), —$XR_C$, and Y;

$R_C$ and $R_D$, are the same or different, and are independently selected at each occurrence from: hydrogen, and straight, branched, and cyclic alkyl groups, and (cycloalkyl)alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, mono- or di-($C_1$–$C_4$alkyl) amino, —NHC(=O)($C_1$–$C_6$alkyl), —N($C_1$–$C_6$alkyl)C (=O)($C_1$–$C_6$alkyl), —NHS(O)$_n$($C_1$–$C_6$alkyl), —S(O)$_n$ ($C_1$–$C_6$alkyl), —S(O)$_n$NH($C_1$–$C_6$alkyl), —S(O)$_n$N ($C_1$–$C_6$alkyl)($C_1$–$C_6$alkyl), and Z;

X is independently selected at each occurrence from the group consisting of —CH$_2$—, —CHR$_D$—, —O—, —C(=O), —C(=O)O—, —S(O)$_n$—, —NH—, —NR$_D$—, —C(=O)NH—, —C(=O)NR$_D$—, —S(O)$_n$ NH—; —S(O)$_n$NR$_D$—, —OC(=S)S—, —NHC(=O)—, —NR$_D$C(=O)—, —NHS(O)$_n$—, and —NR$_D$S(O)$_n$—;

Y and Z are independently selected at each occurrence from: 3- to 7-membered carbocyclic or heterocyclic groups, which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, and —S(O)$_n$(alkyl), wherein said 3- to 7-membered heterocyclic groups contain from 1 to 3 heteroatom(s) independently selected from N, O, and S, with remaining ring members being carbon; and n is independently selected at each occurrence from 0, 1, and 2.

2. A compound or salt according to claim 1, wherein:

R is absent;

$R_1$ and $R_2$ are independently selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii) $C_1$–$C_3$haloalkyl, and ix) $C_1$–$C_3$haloalkoxy wherein each of iii, iv, v, vi, and vii is unsubstituted or substituted by 1–3 groups independently chosen from hydroxy, amino, cyano, and halogen.

3. A compound or salt according to claim 1 wherein:

R is absent; and $R_C$ and $R_D$, which may be the same or different, are independently selected at each occurrence from straight, branched, or cyclic alkyl groups having from 1 to 8 carbon atoms, which alkyl groups may contain one or more double or triple bonds.

4. A compound or salt according to claim 3, wherein:

$R_1$ and $R_2$ are independently selected from the group consisting of i) hydrogen, ii) halogen, iii) $C_1$–$C_3$alkyl, iv) $C_1$–$C_3$alkoxy, v) ($C_3$–$C_7$cycloalkyl)$C_0$–$C_3$alkyl, vi) ($C_3$–$C_7$cycloalkyl)$C_0$–$C_3$alkoxy, vii) mono- or di-($C_1$–$C_3$alkyl)amino, viii) $C_1$–$C_3$haloalkyl, and ix) $C_1$–$C_3$haloalkoxy wherein each of iii, iv, v, vi, and vii is unsubstituted or substituted by 1–3 groups independently chosen from hydroxy, amino, cyano, and halogen.

5. A compound or salt according to claim 1, wherein
R is absent;
$Z_2$ is $CR_2$ and $Z_3$ is nitrogen; and
$Ar_1$ is chosen from phenyl which is mono-, di-, or tri-substituted with $R_A$, and 1-naphthyl, 2-naphthyl, pyridyl, pyrimidinyl, pyrazinyl, pyrimidinyl, thienyl, thiazolyl, pyrazolyl, imidazolyl, tetrazolyl, oxazolyl, isoxazolyl, pyrrolyl, furanyl, and triazolyl, each of which is optionally mono-, di-, or tri-substituted with $R_A$.

6. A compound or salt according to claim 5, wherein:
$R_1$ and $R_2$ are independently selected from hydrogen, cyano, amino, halogen, $C_1$–$C_6$alkyl, $C_1$–$C_6$alkoxy, $(C_3$–$C_7$cycloalkyl)$C_0$–$C_3$alkyl, $(C_3$–$C_7$cycloalkyl)$C_0$–$C_3$alkoxy, mono- or di-$(C_1$–$C_6$alkyl)amino, $C_1$–$C_6$haloalkyl, $C_1$–$C_6$haloalkoxy, and —$SO_n$($C_1$–$C_6$alkyl);
$R_A$ is independently selected at each occurrence from
i) halogen, cyano, nitro, halo($C_1$–$C_6$)alkyl, halo($C_1$–$C_6$)alkoxy, hydroxy, amino, $C_1$–$C_6$alkyl, $C_2$–$C_6$alkenyl, $C_2$–$C_6$alkynyl, $C_3$–$C_7$cycloalkyl, $(C_3$–$C_7$cycloalkyl)$C_1$–$C_4$alkyl, $C_1$–$C_6$alkoxy, mono- or di-$(C_1$–$C_6$alkyl)amino, —CHO, and —C(=O)$CH_3$;
ii) $C_1$–$C_6$alkoxy and $C_1$–$C_6$ alkyl which are unsubstituted or substituted with 1 or 2 groups independently selected from halogen, hydroxy, cyano, amino, oxo, $C_1$–$C_4$alkoxy, mono- or di-$(C_1$–$C_6$alkyl)amino, halo$(C_1$–$C_4)$alkyl, halo($C_1$–$C_4$)alkoxy, $C_1$–$C_4$alkanoyl, morpholinyl, piperazinyl, piperidinyl, furanyl, and pyrrolidinyl, and
iii) 3- to 7-membered carbocyclic or heterocyclic groups which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, and mono- or di-$(C_1$–$C_4$alkyl)amino; and
n is 0, 1, or 2.

7. A compound or salt according to claim 6, wherein:
$R_1$ and $R_2$ are independently selected from the group consisting of hydrogen, halogen, $C_1$–$C_4$alkyl, $C_1$–$C_3$alkoxy, $(C_3$–$C_7$cycloalkyl)$C_0$–$C_3$alkyl, $(C_3$–$C_7$cycloalkyl)$C_0$–$C_3$alkoxy, mono- or di-$(C_1$–$C_3$alkyl)amino, $C_1$–$C_3$haloalkyl, and $C_1$–$C_3$haloalkoxy; and
$Ar_1$ is selected from the group consisting of phenyl which is mono- di- or trisubstituted, and 1-naphthyl, 2-naphthyl, pyridyl, pyrimidinyl, pyrazolyl, imidazolyl, tetrazolyl, and pyrazinyl, each of which is optionally mono- di- or trisubstituted with $R_A$.

8. A compound or salt according to claim 7, of Formula VI

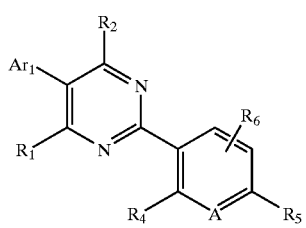

Formula VI wherein:
A is nitrogen or CH;
$R_1$ and $R_2$ are independently chosen from hydrogen, halogen, methyl, ethyl, methoxy, ethoxy, trifluoromethyl, trifluoromethoxy, and methylamino;

$R_4$ and $R_5$, are independently chosen from halogen, halo($C_1$–$C_2$)alkyl, halo($C_1$–$C_2$)alkoxy, hydroxy, amino, $C_1$–$C_3$alkyl, $C_1$–$C_2$alkoxy, and mono- or di-$(C_1$–$C_2$alkyl)amino;
$R_6$ is chosen from hydrogen, halogen, halo($C_1$–$C_2$)alkyl, halo($C_1$–$C_2$)alkoxy, hydroxy, amino, $C_3$–$C_3$alkyl, $C_1$–$C_2$alkoxy, and mono- or di-$(C_1$–$C_2$alkyl)amino.

9. A compound or salt according to claim 8 of Formula VII

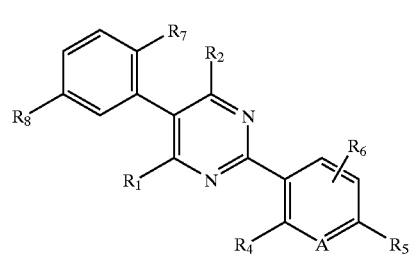

Formula VII wherein $R^7$ and $R^8$ are independently chosen from methyl, ethyl, methoxy, ethoxy, trifluoromethyl, trifluoromethoxy, and halogen.

10. A compound according to claim 1 which is 4-Fluoro-1-methoxy-2-[4methoxy-2-(6-methoxy-2,4-dimethylphenyl)-6-methylpyrimidin-5-yl]benzene; or a pharmaceutically acceptable salt thereof.

11. A compound or salt according to claim 1 wherein, in a standard in vitro CRF receptor binding assay the compound exhibits an $IC_{50}$ value for CRF receptors of less than or equal to 1 micromolar.

12. A compound or salt according to claim 1 wherein, in a standard in vitro CRF receptor binding assay the compound exhibits an $IC_{50}$ value for CRF receptors of less than or equal to 100 nanomolar.

13. A compound or salt according to claims 1 wherein, in a standard in vitro CRF receptor binding assay, the compound exhibits an $IC_{50}$ value for CRF receptors of less than or equal to 10 nanomolar.

14. A compound of Formula I

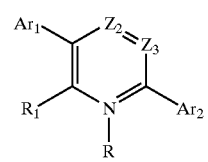

Formula I or a pharmaceutically acceptable salt thereof, wherein:
R is oxygen or absent;
$Z_2$ is $CR_2$;
$Z_3$ is nitrogen;
$Ar_1$ is selected from the group consisting of:
phenyl which is mono-, di-, or tri-substituted with $R_A$, and
1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, and triazolyl, each of which is optionally mono-, di-, or tri-substituted with $R_A$;
$Ar_2$ is 1-naphthyl, 2-naphthyl, pyridyl, pyrimidinyl, pyrazinyl, pyridizinyl, thienyl, thiazolyl, pyrazolyl, imidazolyl, tetrazolyl, oxazolyl, isoxazolyl, pyrrolyl, furanyl, and triazolyl, each of which is optionally mono-, di-, or tri-substituted with $R_A$;

$R_1$ and $R_2$ are independently selected from hydrogen, halogen, hydroxy, cyano, amino, nitro, $C_1$–$C_6$alkyl$_1$, $C_1$–$C_6$alkyl$_1$—O—, mono- or di-($C_1$–$C_6$alkyl$_1$)amino, $C_3$–$C_7$cycloalkyl$_2$($C_0$–$C_4$alkyl$_1$), $C_3$–$C_7$cycloalkenyl$_2$ ($C_0$–$C_4$alkyl$l_1$), $C_3$–$C_7$cycloalkyl$_2$($C_0$–$C_4$alkyl$_1$)—O—, $C_3$–$C_7$cycloalkenyl$_2$($C_0$–$C_4$alkyl$_1$)—O—, halo$C_1$–$C_6$alkyl$_1$, halo$C_1$–$C_6$akyl$_1$—O—, and —S(O)$_n$ ($C_1$–$C_6$alkyl$_1$), where each alkyl$_1$ is independently straight or branched, contains 0 or 1 or more double or triple bonds, and is unsubstituted or substituted with one or more substituents independently chosen from halogen, hydroxy, oxo, cyano, $C_1$–$C_4$alkoxy, amino, and mono- or di-($C_1$–$C_4$alkyl)amino, and where each $C_3$–$C_7$cycloalkyl$_2$ and $C_3$–$C_7$cycloalkenyl$_2$ is optionally substituted by one or more substituents independently chosen from halogen, hydroxy, oxo, cyano, $C_1$–$C_4$alkoxy, amino, and mono- or di-($C_1$–$C_4$)alkylamino, with the proviso that at least one of $R_1$ and $R_2$ is not hydrogen;

$R_A$ is independently selected at each occurrence from halogen, cyano, nitro, halo($C_1$–$C_6$)alkyl, halo($C_1$–$C_6$) alkoxy, hydroxy, amino, $C_1$–$C_6$alkyl substituted with 0–2 $R_B$, $C_2$–$C_6$alkenyl substituted with 0–2 $R_B$, $C_2$–$C_6$alkynyl substituted with 0–2 $R_B$, $C_3$–$C_7$cycloalkyl substituted with 0–2 $R_B$, ($C_3$–$C_7$cycloalkyl)$C_1$–$C_4$alkyl substituted with 0–2 $R_B$, $C_1$–$C_6$alkoxy substituted with 0–2 $R_B$, —NH($C_1$–$C_6$alkyl) substituted with 0–2 $R_B$, —N($C_1$–$C_6$alkyl)($C_1$–$C_6$alkyl) where each $C_1$–$C_6$alkyl is independently substituted with 0–2 $R_B$, —X$R_C$, and Y;

$R_B$ is independently selected at each occurrence from halogen, hydroxy, cyano, amino, $C_1$–$C_4$alkyl, $C_1$–$C_4$alkoxy, mono- or di-($C_1$–$C_4$alkyl)amino, —S(O)$_n$(alkyl), halo($C_1$–$C_4$)alkyl, halo($C_1$–$C_4$)alkoxy, —CO($C_1$–$C_4$alkyl), —CONH($C_1$–$C_4$alkyl), —CON($C_1$–$C_4$alkyl)($C_1$–$C_4$alkyl), —X$R_C$, and Y;

$R_C$ and $R_D$, are the same or different, and are independently selected at each occurrence from: hydrogen, and straight, branched, and cyclic alkyl groups, and (cycloalkyl)alkyl groups, having 1 to 8 carbon atoms, and containing zero or one or more double or triple bonds, each of which 1 to 8 carbon atoms may be further substituted with one or more substituent(s) independently selected from oxo, hydroxy, halogen, cyano, amino, $C_1$–$C_6$alkoxy, mono- or di-($C_1$–$C_4$alkyl) amino, —NHC(=O)($C_1$$C_6$alkyl) —N($C_1$–$C_6$alkyl)C (=O)($C_1$–$C_6$alkyl), —S(O)$_n$N($C_1$–$C_6$alkyl)($C_1$–$C_6$alkyl) and Z;

X is independently selected at each occurrence from the group consisting of —CH$_2$—, —CHR$_D$—, —O—, —C(=O)—, —C(=O)O—, —S(O)$_n$—, —NH—, —NR$_D$—, —C(=O)NH—, —C(=O)NR$_D$—, —S(O)$_n$NH—, —S(O)$_n$NR$_D$—, —OC(=S)S—, —NHC (=O)—, —NR$_D$C(=O)—, —NHS(O)$_n$—, and —NR$_D$S(O)$_n$—;

Y and Z are independently selected at each occurrence from: 3- to 7-membered carbocyclic or heterocyclic groups, which are saturated, partially unsaturated, or aromatic, which may be further substituted with one or more substituents independently selected from halogen, oxo, hydroxy, amino, cyano, $C_1$–$C_4$alkyl, $C_1$–$C_4$alkoxy, mono- or di-($C_1$–$C_4$alkyl)amino, and —S(O)$_n$(alkyl), wherein said 3- to 7-membered heterocyclic groups contain from 1 to 3 heteroatom(s) independently selected from N, O, and S, with remaining ring members being carbon; and n is independently selected at each occurrence from 0, 1, and 2.

15. A pharmaceutical composition comprising a pharmaceutically acceptable carrier and a compound or salt of claim 1.

16. A pharmaceutical composition according to claim 15, wherein the composition is formulated as an injectable fluid, an aerosol, a cream, a gel, a pill, a capsule, a syrup or a transdermal patch.

17. A package comprising a pharmaceutical composition of claim 15 in a container and further comprising indicia comprising at least one of:

instructions for using the composition to treat a patient suffering from anxiety, or instructions or using the composition to treat a patient suffering from stress, or instructions for using the composition to treat a patient suffering from depression.

18. A package comprising a pharmaceutical composition of claim 15 in a container and further comprising at least one of: instructions for using the composition to treat a patient suffering from irritable bowel syndrome or instructions for using the composition to treat a patient suffering from Crohn's disease.

19. A method for treating depression comprising administering to a patient in need of such treatment a therapeutically effective amount of a compound or salt according to claim 1.

20. A method of inhibiting the binding of CRF to a CRF1 Receptor, which method comprises:

contacting a solution comprising CRF and a compound or salt of claim 1 with a cell expressing the CRF receptor, wherein the compound or salt is present in the solution at a concentration sufficient to inhibit in vitro CRF binding to IMR32 cell.

21. The method of claim 20 wherein the cell expressing the CRF receptor is a neuronal cell that is contacted in vivo in an animal, and wherein the solution is a body fluid of said animal.

* * * * *